United States Patent
Mangion et al.

(10) Patent No.: US 9,040,526 B2
(45) Date of Patent: May 26, 2015

(54) BENZYLPYRROLIDINONE DERIVATIVES AS MODULATORS OF CHEMOKINE RECEPTOR ACTIVITY

(75) Inventors: Ian K. Mangion, Cranford, NJ (US);
Percy H. Carter, Princeton, NJ (US);
Jingwu Duan, Yardley, PA (US);
Andrew J. Tebben, New Hope, PA (US)

(73) Assignee: Bristol-Myers Squibb Company, Princeton, NJ (US)

( * ) Notice: Subject to any disclaimer, the term of this patent is extended or adjusted under 35 U.S.C. 154(b) by 213 days.

(21) Appl. No.: 13/576,706

(22) PCT Filed: Feb. 8, 2011

(86) PCT No.: PCT/US2011/024014
§ 371 (c)(1),
(2), (4) Date: Aug. 2, 2012

(87) PCT Pub. No.: WO2011/100227
PCT Pub. Date: Aug. 18, 2011

(65) Prior Publication Data
US 2012/0295899 A1   Nov. 22, 2012

Related U.S. Application Data

(60) Provisional application No. 61/302,585, filed on Feb. 9, 2010.

(51) Int. Cl.
*A61K 31/5365* (2006.01)
*C07D 498/04* (2006.01)
*C07D 207/27* (2006.01)

(52) U.S. Cl.
CPC ............ *C07D 498/04* (2013.01); *C07D 207/27* (2013.01)

(58) Field of Classification Search
USPC .......................................... 544/89; 514/230.2
See application file for complete search history.

(56) References Cited

U.S. PATENT DOCUMENTS

2004/0167156 A1   8/2004   Jiao et al.
2007/0238723 A1   10/2007   Goble et al.

FOREIGN PATENT DOCUMENTS

WO   WO/2004/082616 A2   9/2004
WO   WO2004/092124 A2   10/2004
WO   WO2004/110376 A2   12/2004
WO   WO2005/021500 A1   3/2005
WO   WO2005/105092 A2   11/2005

OTHER PUBLICATIONS

Carter, Percy H., "Chemokine receptor antagonism as an approach to anti-inflammatory therapy: 'just right' or plain wrong?", Current Opinion in Chemical Biology, vol. 6, pp. 510-525 (2002).
Premack, et al., "Chemokine receptors: Gateways to inflammation and infection" Nature Medicine, vol. 2 (11), pp. 1174-1178 (1996).
Saunders, et al., "Opportunities for novel therapeutic agents acting at chemokine receptors" Drug Discovery Today, vol. 4(2), pp. 80-92 (1999).
Trivedi, et al., "Section IV. Immunology, Endocrinology and Metabolic Diseases. Chapter 17. Chemokines: Targets for Novel Therapeutics", Annual Reports in Medicinal Chemistry, vol. 35, pp. 191-200 (2000).
Yang, et al., "Discovery of 3-Piperidinyl-1-cyclopentane-carboxamide as a Novel Scaffold for Highly Potent CC Chemokine Receptor 2 Antagonists", J. Med. Chem., vol. 50, pp. 2609-2611 (2007).

*Primary Examiner* — Kahsay Habte
(74) *Attorney, Agent, or Firm* — Elliott Korsen

(57) ABSTRACT

The present application describes modulators of MCP-1 or CCR-2 of formula

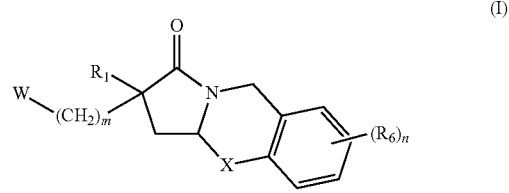

(I)

or stereoisomers or prodrugs or pharmaceutically acceptable salts thereof, wherein m, n, W, X, $R^1$ and $R^6$, are defined herein. In addition, methods of treating and preventing inflammatory diseases such as asthma and allergic diseases, as well as autoimmune pathologies such as rheumatoid arthritis and transplant rejection using modulators of formula (I) are disclosed.

12 Claims, No Drawings

BENZYLPYRROLIDINONE DERIVATIVES AS MODULATORS OF CHEMOKINE RECEPTOR ACTIVITY

CROSS-REFERENCE TO RELATED APPLICATIONS

The present application is a 371 application of PCT/US2011/024014 filed Feb. 8, 2011, which claims priority benefit of U.S. provisional applications Ser. No. 61/302,585, filed Feb. 9, 2010, each of which is incorporated herein by reference in its entirety.

FIELD OF THE INVENTION

This invention relates generally to modulators of chemokine receptor activity, in particular, benzylpyrrolidinone, pharmaceutical compositions containing the same, and methods of using the same as agents for treatment and prevention of inflammatory diseases, allergic and autoimmune diseases, and in particular, rheumatoid arthritis and transplant rejection.

BACKGROUND OF THE INVENTION

Chemokines are chemotactic cytokines, of molecular weight 6-15 kDa, that are released by a wide variety of cells to attract and activate, among other cell types, monocytes, macrophages, T and B lymphocytes, eosinophils, basophils and neutrophils (reviewed in: Luster, *New Eng. J. Med.* 1998, 338, 436-445 and Rollins, *Blood* 1997, 90, 909-928). There are two major classes of chemokines, CXC and CC, depending on whether the first two cysteines in the amino acid sequence are separated by a single amino acid (CXC) or are adjacent (CC). The CXC chemokines, such as interleukin-8 (IL-8), neutrophil-activating protein-2 (NAP-2) and melanoma growth stimulatory activity protein (MGSA) are chemotactic primarily for neutrophils and T lymphocytes, whereas the CC chemokines, such as RANTES, MIP-1α, MIP-1β, the monocyte chemotactic proteins (MCP-1, MCP-2, MCP-3, MCP-4, and MCP-5) and the eotaxins (-1 and -2) are chemotactic for, among other cell types, macrophages, T lymphocytes, eosinophils, dendritic cells, and basophils. There also exist the chemokines lymphotactin-1, lymphotactin-2 (both C chemokines), and fractalkine (a $CX_3C$ chemokine) that do not fall into either of the major chemokine sub-families.

The chemokines bind to specific cell-surface receptors belonging to the family of G-protein-coupled seven-transmembrane-domain proteins (reviewed in: Horuk, *Trends Pharm. Sci.* 1994, 15, 159-165) which are termed "chemokine receptors." On binding their cognate ligands, chemokine receptors transduce an intracellular signal though the associated trimeric G proteins, resulting in, among other responses, a rapid increase in intracellular calcium concentration, changes in cell shape, increased expression of cellular adhesion molecules, degranulation, and promotion of cell migration. There are at least ten human chemokine receptors that bind or respond to CC chemokines with the following characteristic patterns (reviewed in Zlotnik et al., *Immunity* 2000, 12, 121): CCR-1 (or "CKR-1" or "CC-CKR-1") [MIP-1α, MCP-3, MCP-4, RANTES](Neote et al., *Cell* 1993, 72, 415-425, and Luster, *New Eng. J. Med.* 1998, 338, 436-445); CCR-2A and CCR-2B (or "CKR-2A"/"CKR-2B" or "CC-CKR-2A"/"CC-CKR-2B") [MCP-1, MCP-2, MCP-3, MCP-4, MCP-5](Charo et al., *Proc. Natl. Acad. Sci. USA* 1994, 91, 2752-2756, and Luster, *New Eng. J. Med.* 1998, 338, 436-445); CCR-3 (or "CKR-3" or "CC-CKR-3") [eotaxin-1, eotaxin-2, RANTES, MCP-3, MCP-4](Combadiere et al., *J. Biol. Chem.* 1995, 270, 16491-16494, and Luster, *New Eng. J. Med.* 1998, 338, 436-445); CCR-4 (or "CKR-4" or "CC-CKR-4") [TARC, MDC](Power et al., *J. Biol. Chem.* 1995, 270, 19495-19500, and Luster, *New Eng. J. Med.* 1998, 338, 436-445); CCR-5 (or "CKR-5" OR "CC-CKR-5") [MIP-1α, RANTES, MIP-1β](Samson et al., *Biochemistry* 1996, 35, 3362-3367); CCR-6 (or "CKR-6" or "CC-CKR-6") [LARC] (Baba et al., *J. Biol. Chem.* 1997, 272, 14893-14898); CCR-7 (or "CKR-7" or "CC-CKR-7") [ELC] (Yoshie et al., *J. Leukoc. Biol.* 1997, 62, 634-644); CCR-8 (or "CKR-8" or "CC-CKR-8") [1-309](Napolitano et al., *J. Immunol.*, 1996, 157, 2759-2763); CCR-10 (or "CKR-10" or "CC-CKR-10") [MCP-1, MCP-3](Bonini et al., *DNA Cell Biol.* 1997, 16, 1249-1256); and CCR-11 [MCP-1, MCP-2, and MCP-4] (Schweickart et al., *J. Biol. Chem.* 2000, 275, 9550).

In addition to the mammalian chemokine receptors, mammalian cytomegaloviruses, herpesviruses and poxviruses have been shown to express, in infected cells, proteins with the binding properties of chemokine receptors (reviewed in: Wells et al., *Curr. Opin. Biotech.* 1997, 8, 741-748). Human CC chemokines, such as RANTES and MCP-3, can cause rapid mobilization of calcium via these virally encoded receptors. Receptor expression may be permissive for infection by allowing for the subversion of normal immune system surveillance and response to infection. Additionally, human chemokine receptors, such as CXCR4, CCR2, CCR3, CCR5 and CCR8, can act as co-receptors for the infection of mammalian cells by microbes as with, for example, the human immunodeficiency viruses (HIV).

The chemokines and their cognate receptors have been implicated as being important mediators of inflammatory, infectious, and immunoregulatory disorders and diseases, including asthma and allergic diseases, as well as autoimmune pathologies such as rheumatoid arthritis and atherosclerosis (reviewed in: Carter, P. H., *Curr. Opin. Chem. Biol.* 2002, 6, 510; Trivedi et al., *Ann. Reports Med. Chem.* 2000, 35, 191; Saunders et al., *Drug Disc. Today* 1999, 4, 80; Premack et al., *Nature Medicine* 1996, 2, 1174). For example, the chemokine macrophage inflammatory protein-1 (MIP-1α) and its receptor CC Chemokine Receptor 1 (CCR-1) play a pivotal role in attracting leukocytes to sites of inflammation and in subsequently activating these cells. When the chemokine MIP-1α binds to CCR-1, it induces a rapid increase in intracellular calcium concentration, increased expression of cellular adhesion molecules, cellular degranulation, and the promotion of leukocyte migration.

In addition, demonstration of the chemotactic properties of MIP-1α in humans has been provided experimentally. Human subjects, when injected intradermally with MTP-1α, experienced a rapid and significant influx of leukocytes to the site of injection (Brummet, M. E., *J. Immun.* 2000, 164, 3392-3401).

The chemokines and their cognate receptors have been implicated as being important mediators of inflammatory, infectious, and immunoregulatory disorders and diseases, including asthma and allergic diseases; as well as autoimmune pathologies, such as rheumatoid arthritis and multiple sclerosis; and metabolic diseases, such as atherosclerosis and diabetes (reviewed in: Charo et al., *New Eng. J. Med.* 2006, 354, 610-621; Gao, Z. et al., *Chem. Rev.* 2003, 103, 3733; Carter, P. H., *Curr. Opin. Chem. Biol.* 2002, 6, 510; Trivedi et al., *Ann. Reports Med. Chem.* 2000, 35, 191; Saunders et al., *Drug Disc. Today* 1999, 4, 80; Premack et al., *Nature Medicine* 1996, 2, 1174). For example, the chemokine monocyte chemoattractant-1 (MCP-1) and its receptor CC Chemokine Receptor 2 (CCR-2) plays a pivotal role in attracting leukocytes to sites of inflammation and in subsequently activating these cells. When the chemokine MCP-1 binds to CCR-2, it induces a rapid increase in intracellular calcium concentration, increased expression of cellular adhesion molecules, and the promotion of leukocyte migration. Demonstration of the importance of the MCP-1/CCR-2 interaction has been provided by experiments with genetically modified mice. MCP-1−/− mice were unable to recruit monocytes into sites of inflammation after several different types of immune challenge (Lu, B. et al., *J. Exp. Med.* 1998, 187, 601). Likewise, CCR-2−/− mice were unable to recruit monocytes or produce interferon-γ when challenged with various exogenous agents; moreover, the leukocytes of CCR-2 null mice did not migrate in response to MCP-1 (Boring, L. et al., *J. Clin. Invest.* 1997, 100, 2552), thereby demonstrating the specificity of the MCP-1/CCR-2 interaction. Two other groups have independently reported equivalent results with different strains of CCR-2−/− mice (Kuziel, W. A. et al., *Proc. Natl. Acad. Sci. USA* 1997, 94, 12053, and Kurihara, T. et al., *J. Exp. Med.* 1997, 186, 1757). The viability and generally normal health of the MCP-1−/− and CCR-2−/− animals is noteworthy, in that disruption of the MCP-1/CCR-2 interaction does not induce physiological crisis. Taken together, these data lead one to the conclusion that molecules that block the actions of MCP-1/CCR2 would be useful in treating a number of inflammatory and autoimmune disorders (reviewed in: Feria, M. et al., *Exp. Opin. Ther. Patents* 2006, 16, 49; and Dawson, J. et al., *Exp. Opin. Ther. Targets* 2003, 7, 35). This hypothesis has now been validated in a number of different animal disease models, as described below.

It is known that MIP-1α is elevated in the synovial fluid and blood of patients with rheumatoid arthritis (Koch, A. et al., *J. Clin. Invest.* 1994, 93, 921-928). Moreover, several studies have demonstrated the potential therapeutic value of antagonism of the MIP-1α/CCR1 interaction in treating rheumatoid arthritis (Pease, J. E. et al., *Expert Opin. Invest. Drugs* 2005, 14, 785-796).

An antibody to MIP-1α was shown to ameliorate experimental autoimmune encepahlomytis (EAE), a model of multiple sclerosis, in mice (Karpus, W. J. et al., *J. Immun.* 1995, 5003-5010). Likewise, inflammatory disease symptoms could be controlled via direct administration of antibodies for MIP-1α to mice with collagen-induced arthritis (Lukacs, N. W. et al., *J. Clin. Invest.* 1995, 95, 2868-2876).

It is known that MCP-1 is upregulated in patients who develop bronchiolitis obliterans syndrome after lung transplantation (Reynaud-Gaubert, M. et al., *J. Heart Lung Transplant.*, 2002, 21, 721-730; Belperio, B. et al., *J. Clin. Invest.* 2001, 108, 547-556). In a murine model of bronchiolitis obliterans syndrome, administration of an antibody to MCP-1 led to attenuation of airway obliteration; likewise, CCR2−/− mice were resistant to airway obliteration in this same model (Belperio, J. et al., *J. Clin. Invest.* 2001, 108, 547-556). These data suggest that antagonism of MCP-1/CCR2 may be beneficial in treating rejection of organs following transplantation. In addition, studies have shown that disruption of MCP-1/CCR2 axis was able to prolong the survival of islet transplant (Lee, I. et al., *J. Immunol.* 2003, 171, 6929; Abdi, R. et al., *J. Immunol.* 2004, 172, 767). In rat graft models, CCR2 and MCP-1 was shown to be upregulated in grafts that develop graft vasculopathy (Horiguchi, K. et al., *J. Heart Lung Transplant.* 2002, 21, 1090). In another study, anti-MCP-1 gene therapy attenuated graft vasculopathy (Saiura, A. et al., *Arterioscler. Thromb. Vasc. Biol.* 2004, 24, 1886). One study described inhibition of experimental vein graft neoinitimal formation by blockage of MCP-1 (Tatewaki, H. et al., *J. Vasc. Surg.* 2007, 45, 1236).

Other studies have demonstrated the potential therapeutic value of antagonism of the MCP-1/CCR2 interaction in treating asthma. Sequestration of MCP-1 with a neutralizing antibody in ovalbumin-challenged mice resulted in marked decrease in bronchial hyperresponsiveness and inflammation (Gonzalo, J-A. et al., *J. Exp. Med.* 1998, 188, 157). It proved possible to reduce allergic airway inflammation in *Schistosoma mansoni* egg-challenged mice through the administration of antibodies for MCP-1 (Lukacs, N. W. et al., *J. immunol.* 1997, 158, 4398). Consistent with this, MCP-1−/− mice displayed a reduced response to challenge with *Schistosoma mansoni* egg (Lu, B. et al., *J. Exp. Med.* 1998, 187, 601).

Other studies have demonstrated the potential therapeutic value of antagonism of the MCP-1/CCR2 interaction in treating kidney disease. Administration of antibodies for MCP-1 in a murine model of glomerularnephritis resulted in a marked decrease in glomerular crescent formation and deposition of type I collagen (Lloyd, C. M. et al., *J. Exp. Med.* 1997, 185, 1371). In addition, MCP-1−/− mice with induced nephrotoxic serum nephritis showed significantly less tubular damage than their MCP-1+/+counterparts (Tesch, G. H. et al., *J. Clin. Invest.* 1999, 103, 73).

Several studies have demonstrated the potential therapeutic value of antagonism of the MCP-1/CCR2 interaction in treating systemic lupus erythematosus. CCR2−/− mice exhibited prolonged survival and reduced renal disease relative to their WT counterparts in a murine model of systemic lupus erythematosus (Perez de Lema, G. et al. *J. Am. Soc. Neph.* 2005, 16, 3592). These data are consistent with the disease-modifying activity found in recent studies on genetic deletion of MCP-1 (Shimizu, S. et al. *Rheumatology (Oxford)* 2004, 43, 1121; Tesch, G. H. et al., *J. Exp. Med.* 1999, 190, 1813) or administration of a peptide antagonist of CCR2 (Hasegawa, H. et al. *Arthritis & Rheumatism* 2003, 48, 2555) in rodent models of lupus.

A remarkable 30-fold increase in $CCR2^+$ lamina propria lymphocytes was observed in the small bowels from Crohn's patients relative to non-diseased ileum (Connor, S. J. et al., *Gut* 2004, 53, 1287). Also of note, there was an expansion in the subset of circulating $CCR2^+/CD14^+/CD56^+$ monocytes in patients with active Crohn's disease relative to controls. Several rodent studies have demonstrated the potential therapeutic value of antagonism of the MCP-1/CCR2 interaction in treating Crohn's disease/colitis. CCR-2−/− mice were protected from the effects of dextran sodium sulfate-induced colitis (Andres, P. G. et al., *J. Immunol.* 2000, 164, 6303). Administration of a small molecule antagonist of CCR2, CCR5, and CXCR3 (murine binding affinities=24, 236, and 369 nM, respectively) also protected against dextran sodium sulfate-induced colitis (Tokuyama, H. et al., *Int. Immunol.* 2005, 17, 1023). Finally, MCP-1−/− mice showed substantially reduced colonic damage (both macroscopic and histological) in a hapten-induced model of colitis (Khan, W. I. et al., *Am. J. Physiol. Gastrointest. Liver Physiol.* 2006, 291, G803).

Two reports described the overexpression of MCP-1 in the intestinal epithelial cells and bowel mucosa of patients with inflammatory bowel disease (Reinecker, H. C. et al., *Gastroenterology* 1995, 108, 40, and Grimm, M. C. et al., *J. Leukoc. Biol.* 1996, 59, 804).

One study described the association of promoter polymorphism in the MCP-1 gene with scleroderma (systemic sclerosis) (Karrer, S. et al., *J. Invest. Dermatol.* 2005, 124, 92). In related models of tissue fibrosis, inhibition of CCR2/MCP-1 axis reduced fibrosis in skin (Yamamoto, T. et al., *J. Invest.*

Dermatol. 2003, 121, 510; Ferreira, A. M. et al., *J. Invest. Dermatol.* 2006, 126, 1900), lung (Okuma, T. et al., *J. Pathol.* 2004, 204, 594; Gharaee-Kermani, M. et al., *Cytokine* 2003, 24, 266), kidney (Kitagawa, K. et al., *Am. J. Pathol.* 2004, 165, 237; Wada, T. et al., *J. Am. Soc. Nephrol.* 2004, 15, 940), heart (Hayashidani, S. et al., *Circulation* 2003, 108, 2134), and liver (Tsuruta, S. et al., *Int. Mol. Med.* 2004, 14, 837).

One study has demonstrated the potential therapeutic value of antagonism of the MCP-1/CCR2 interaction in treating alveolitis. When rats with IgA immune complex lung injury were treated intravenously with antibodies raised against rat MCP-1 (JE), the symptoms of alveolitis were partially alleviated (Jones, M. L. et al., *J. Immunol.* 1992, 149, 2147).

Several studies have shown the potential therapeutic value of antagonism of the MCP-1/CCR2 interaction in treating cancer (reviewed in: Craig, M. J. et al., *Cancer Metastasis Rev.* 2006, 25, 611; Conti, I., *Seminars in Cancer Biology* 2004, 14, 149; Giles, R., *Curr. Cancer Drug Targets* 2006, 6, 659). When immunodeficient mice bearing human breast carcinoma cells were treated with an anti-MCP-1 antibody, inhibition of lung micrometastases and increases in survival were observed (Salcedo, R. et al., *Blood* 2000, 96, 34-40). Using human clinical tumor specimens, CCR2 expression was associated with prostrate cancer progression (Lu, Y. et al., *J. Cell. Biochem.* 2007, 101, 676). In vitro, MCP-1 expression has been shown to mediate prostrate cancer cell growth and invasion (Lu, Y. et al., *Prostate* 2006, 66, 1311); furthermore, MCP-1 expressed by prostate cancer cells induced human bone marrow progenitors for bone resorption (Lu, Y. et al., *Cancer Res.* 2007, 67, 3646).

Multiple studies have described the potential therapeutic value of antagonism of the MCP-1/CCR2 interaction in treating restenosis. In humans, MCP-1 levels correlate directly with risk for restenosis (Cipollone, F. et al., *Arterioscler. Thromb. Vasc. Biol.* 2001, 21, 327). Mice deficient in CCR2 or in MCP-1 showed reductions in the intimal area and in the intima/media ratio (relative to wildtype littermates) after arterial injury (Roque, M. et al., *Arterioscler. Thromb. Vasc. Biol.* 2002, 22, 554; Schober, A. et al., *Circ. Res.* 2004, 95, 1125; Kim, W. J. et al., *Biochem Biophys. Res. Commun.* 2003, 310, 936). In mice, transfection of a dominant negative inhibitor of MCP-1 in the skeletal muscle (Egashira, K. et al., *Circ. Res.* 2002, 90, 1167) also reduced intimal hyperplasia after arterial injury. Blockade of CCR2 using a neutralizing antibody reduced neointimal hyperplasia after stenting in primates (Horvath, C. et al., *Circ. Res.* 2002, 90, 488).

Two reports describe the overexpression of MCP-1 rats with induced brain trauma (King, J. S. et al., *J. Neuroimmunol.* 1994, 56, 127, and Berman, J. W. et al., *J. Immunol.* 1996, 156, 3017). In addition, studies have shown that both CCR2−/− (Dimitrijevic, O. B. et al., *Stroke* 2007, 38, 1345) and MCP-1−/− mice (Hughes, P. M. et al., *J. Cereb. Blood Flow Metab.* 2002, 22, 308) are partially protected from ischemia/reperfusion injury.

It is known that monocytes/macrophages play an important role in the development of neuropathic pain (Liu, T. et al., *Pain* 2000, 86, 25). Consistent with this notion, a potential role for CCR2 in the treatment of both inflammatory and neuropathic pain has been described recently. CCR2−/− mice showed altered responses to inflammatory pain relative to their WT counterparts, including reduced pain behavior after intraplantar formalin injection and slightly reduced mechanical allodynia after intraplantar CFA injection (Abbadie, C. et al., *Proc. Natl. Acad. Sci., USA* 2003, 100, 7947). In addition, CCR2−/− mice did not display significant mechanical allodynia after sciatic nerve injury. Likewise, a small molecule CCR2 antagonist reduced mechanical allodynia to ~80% of pre-injury levels after oral administration (Abbadie, C. et al., WO 2004/110376).

One study described the critical role of MCP-1 in ischemic cardiomyopathy (Frangogiannis, N. G. et al., *Circulation* 2007, 115, 584). Another study described the attenuation of experimental heart failure following inhibition of MCP-1 (Hayashidani, S. et al., *Circulation* 2003, 108, 2134).

Other studies have provided evidence that MCP-1 is overexpressed in various disease states not mentioned above. These reports provide correlative evidence that MCP-1 antagonists could be useful therapeutics for such diseases. Another study has demonstrated the overexpression of MCP-1 in rodent cardiac allografts, suggesting a role for MCP-1 in the pathogenesis of transplant arteriosclerosis (Russell, M. E. et al., *Proc. Natl. Acad. Sci. USA* 1993, 90, 6086). The overexpression of MCP-1 has been noted in the lung endothelial cells of patients with idiopathic pulmonary fibrosis (Antoniades, H. N. et al., *Proc. Natl. Acad. Sci. USA* 1992, 89, 5371). Similarly, the overexpression of MCP-1 has been noted in the skin from patients with psoriasis (Deleuran, M. et al., *J. Dermatol. Sci.* 1996, 13, 228, and Gillitzer, R. et al., *J. Invest. Dermatol.* 1993, 101, 127); correlative findings with predominance of CCR2+ cells have also been reported (Vestergaard, C. et al., *Acta Derm. Venerol.* 2004, 84, 353). Finally, a recent report has shown that MCP-1 is overexpressed in the brains and cerebrospinal fluid of patients with HIV-1-associated dementia (Garzino-Demo, A., WO 99/46991).

In addition, CCR2 polymorphism has been shown to be associated with sarcoidosis at least in one subset of patients (Spagnolo, P. et al., *Am. J. Respir. Crit. Care Med.* 2003, 168, 1162).

It should also be noted that CCR-2 has been implicated as a co-receptor for some strains of HIV (Doranz, B. J. et al., *Cell* 1996, 85, 1149). It has also been determined that the use of CCR-2 as an HIV co-receptor can be correlated with disease progression (Connor, R. I. et al., *J. Exp. Med.* 1997, 185, 621). This finding is consistent with the recent finding that the presence of a CCR-2 mutant, CCR2-64I, is positively correlated with delayed onset of HIV in the human population (Smith, M. W. et al., *Science* 1997, 277, 959). Although MCP-1 has not been implicated in these processes, it may be that MCP-1 antagonists that act via binding to CCR-2 may have beneficial therapeutic effects in delaying the disease progression to AIDS in HIV-infected patients.

It should be noted that CCR2 is also the receptor for the human chemokines MCP-2, MCP-3, and MCP-4 (Luster, *New Eng. Med.* 1998, 338, 436-445). Since the new compounds of formula (I) described herein antagonize MCP-1 by binding to the CCR-2 receptor, it may be that these compounds of formula (I) are also effective antagonists of the actions of MCP-2, MCP-3, and MCP-4 that are mediated by CCR-2. Accordingly, when reference is made herein to "antagonism of MCP-1," it is to be assumed that this is equivalent to "antagonism of chemokine stimulation of CCR-2."

SUMMARY OF THE INVENTION

Accordingly, the present invention provides novel antagonists or partial agonists/antagonists of MCP-1 or CCR-2 receptor activity, or pharmaceutically acceptable salts or prodrugs thereof.

The present invention provides pharmaceutical compositions comprising a pharmaceutically acceptable carrier and a therapeutically effective amount of at least one of the compounds of the present invention or a pharmaceutically acceptable salt or prodrug form thereof.

The present invention provides a method for treating rheumatoid arthritis and transplant rejection, comprising administering to a host in need of such treatment a therapeutically effective amount of at least one of the compounds of the present invention or a pharmaceutically acceptable salt or prodrug form thereof.

The present invention provides a method for treating inflammatory diseases, comprising administering to a host in need of such treatment a therapeutically effective amount of at least one of the compounds of the present invention or a pharmaceutically acceptable salt or prodrug form thereof.

The present invention provides novel benzylpyrrolidinonyl derivatives for use in therapy.

The present invention provides the use of novel benzylpyrrolidinonyl derivatives for the manufacture of a medicament for the treatment of inflammatory diseases.

These and other features of the invention, which will become apparent during the following detailed description, have been achieved by the inventors' discovery that compounds of formula (I):

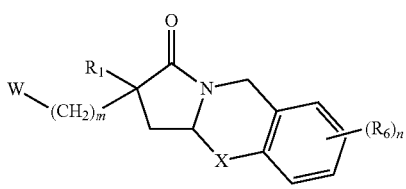

(I)

or stereoisomers or prodrugs or pharmaceutically acceptable salts thereof, wherein m, n, W, X, $R^1$ and $R^6$, are defined below, are effective modulators of MCP-1 and chemokine activity.

DETAILED DESCRIPTION OF THE PRESENT INVENTION

In one embodiment, the present invention provides novel compounds of formula (I):

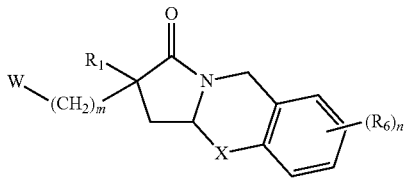

(I)

or a stereoisomer or a pharmaceutically acceptable salt thereof, wherein:

X is O or $CH_2$;

W is a $-NR_2R_3$ or a 3- to 20-membered nitrogen containing ring, wherein the ring is (i) attached through the nitrogen atom, (ii) may optionally contain 1-4 heteroatoms selected from N, O, and S and (iii) be optionally substituted with one or more $R_{10a}$'s;

m is 1-4;

n is 0-2;

$R_1$ is H or alkyl;

$R_2$ is H, alkyl, cycloalkyl, aryl, heteroaryl or heterocyclyl, wherein the cycloalkyl, aryl, heteroaryl or heterocyclyl may be optionally substituted with may be optionally substituted with be optionally substituted with one or more $R_{9a}$'s;

$R_3$ is H, alkyl, cycloalkyl, aryl, heteroaryl or heterocyclyl, wherein the cycloalkyl, aryl, heteroaryl or heterocyclyl may be optionally substituted with may be optionally substituted with be optionally substituted with one or more $R_{9a}$'s;

$R_6$, at each occurrence, is independently selected from halo, alkyl, haloalkyl, haloalkoxy, and aryl optionally substituted with halo;

$R_{9a}$, at each occurrence, is independently selected from alkyl, haloalkyl, aryl, cycloalkyl, heteroaryl, heterocyclyl, halo, $-CN$, $-NO_2$, $-C(=O)OR_{14}$, $-OCF_3$, $-OR_{14}$, $=O$, $-NR_{14}R_{14}$ or arylalkyl;

$R_{10a}$, at each occurrence, is independently selected from alkyl, haloalkyl, aryl, cycloalkyl, heteroaryl, heterocyclyl, halo, $-CN$, $-NO_2$, $-C(=O)OR_{14}$, $-OCF_3$, $-OR_{14}$, $=O$, $-NR_{14}R_{14}$ or arylalkyl, wherein the aryl, cycloalkyl, heteroaryl, and heterocyclyl may be optionally substituted with on or more $R_{14a}$'s;

$R_{14}$, at each occurrence, is independently selected from hydrogen, alkyl, cycloalkyl, aryl, heteroaryl or heterocyclyl, wherein the alkyl, cycloalkyl, aryl, heteroaryl and heterocyclyl may be optionally substituted with be optionally substituted with 0-3 $R_{14a}$;

$R_{14a}$, at each occurrence, is independently selected from alkyl, haloalkyl, aryl, cycloalkyl, heteroaryl, heterocyclyl, halo, $-CN$, $-NO_2$, $-C(=O)OR_{24}$, $-OCF_3$, $-OR_{24}$, $=O$, $-NR_{24}R_{24}$ or arylalkyl; and $R_{24}$, at each occurrence, is independently selected from hydrogen, alkyl, cycloalkyl, aryl, heteroaryl or heterocyclyl.

In another embodiment, compounds of the present invention, or a stereoisomer or pharmaceutically acceptable salt from thereof, are those in which the compound is a compound of formula (Ia):

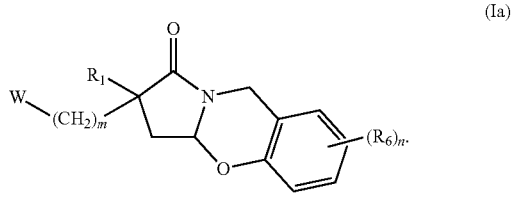

(Ia)

In still yet another embodiment, compounds of the present invention, or a stereoisomer or pharmaceutically acceptable salt from thereof, are those in which:

X is O or $CH_2$;

W is a $-NR_2R_3$ or a 3- to 15-membered nitrogen containing ring, wherein the ring is (i) attached through the nitrogen atom, (ii) may optionally contain 1-4 heteroatoms selected from N, O, and S and (iii) be optionally substituted with one or more $R_{10a}$'s;

m is 1-3;

n is 0-2;

$R_1$ is H or alkyl;

$R_2$ is H, alkyl, cycloalkyl, aryl or heterocyclyl, wherein the cycloalkyl, aryl or heterocyclyl may be optionally substituted with may be optionally substituted with be optionally substituted with one or more $R_{9a}$'s;

$R_3$ is H, alkyl, cycloalkyl, aryl or heterocyclyl, wherein the cycloalkyl, aryl or heterocyclyl may be optionally substituted with may be optionally substituted with be optionally substituted with one or more $R_{9a}$'s;

$R_6$, at each occurrence, is independently selected from halo, alkyl, haloalkyl, haloalkoxy, and aryl optionally substituted with halo;

$R_{9a}$, at each occurrence, is independently selected from alkyl, haloalkyl, aryl, cycloalkyl, heteroaryl, heterocyclyl, halo, —CN, —NO$_2$, —C(=O)OR$_{14}$, —OCF$_3$, —OR$_{14}$, =O, or arylalkyl;

$R_{10a}$, at each occurrence, is independently selected from alkyl, haloalkyl, aryl, cycloalkyl, heteroaryl, heterocyclyl, halo, —CN, —NO$_2$, —C(=O)OR$_{14}$, —OCF$_3$, —OR$_{14}$, =O, or arylalkyl, wherein the aryl, cycloalkyl, heteroaryl, and heterocyclyl may be optionally substituted with on or more $R_{14a}$'s;

$R_{14a}$, at each occurrence, is independently selected from hydrogen, alkyl, cycloalkyl, aryl, heteroaryl or heterocyclyl, wherein the alkyl, cycloalkyl, aryl, heteroaryl and heterocyclyl may be optionally substituted with be optionally substituted with 0-3 $R_{14a}$;

$R_{14a}$, at each occurrence, is independently selected from alkyl, haloalkyl, aryl, cycloalkyl, heteroaryl, heterocyclyl, halo, —CN, —NO$_2$, —C(=O)OR$_{24}$, —OCF$_3$, —OR$_{24}$, =O, or arylalkyl; and $R_{24}$, at each occurrence, is independently selected from hydrogen, alkyl, cycloalkyl, aryl, heteroaryl or heterocyclyl.

In one embodiment, compounds of the present invention, or a stereoisomer or pharmaceutically acceptable salt from thereof, are those in which:

X is O or CH$_2$;

W is a —NR$_2$R$_3$ or a 3- to 12-membered nitrogen containing ring, wherein the ring is (i) attached through the nitrogen atom, (ii) may optionally contain 1-4 heteroatoms selected from N, O, and S and (iii) be optionally substituted with one or more $R_{10a}$'s;

m is 1-2;

n is 1-2;

$R_1$ is H or alkyl;

$R_2$ is H, alkyl or cycloalkyl, wherein the cycloalkyl may be optionally substituted with may be optionally substituted with be optionally substituted with one or more $R_{9a}$'s;

R3 is H, alkyl or cycloalkyl, wherein the cycloalkyl may be optionally substituted with may be optionally substituted with be optionally substituted with one or more $R_{9a}$'s;

$R_6$, at each occurrence, is independently selected from halo, alkyl, haloalkyl, haloalkoxy, and aryl optionally substituted with halo;

$R_{9a}$, at each occurrence, is independently selected from alkyl, haloalkyl, aryl, cycloalkyl, heteroaryl, heterocyclyl, halo, —CN, —NO$_2$, —C(=O)OR$_{14}$, —OCF$_3$, —OR$_{14}$, or arylalkyl;

$R_{10a}$, at each occurrence, is independently selected from alkyl, haloalkyl, aryl, cycloalkyl, heteroaryl, heterocyclyl, halo, —CN, —NO$_2$, —C(=O)OR$_{14}$, —OCF$_3$, —OR$_{14}$, or arylalkyl, wherein the aryl, cycloalkyl, heteroaryl, and heterocyclyl may be optionally substituted with on or more $R_{14a}$'s;

$R_{14}$, at each occurrence, is independently selected from hydrogen, alkyl, cycloalkyl, aryl or heteroaryl, wherein the alkyl, cycloalkyl, aryl and heteroaryl may be optionally substituted with be optionally substituted with 0-3 $R_{14a}$;

$R_{14a}$, at each occurrence, is independently selected from alkyl, haloalkyl, aryl, cycloalkyl, heteroaryl, heterocyclyl, halo, —CN, —NO$_2$, —C(=O)OR$_{24}$, —OCF$_3$, —OR$_{24}$ or arylalkyl; and $R_{24}$, at each occurrence, is independently selected from hydrogen, alkyl, cycloalkyl, aryl or heteroaryl.

In another embodiment, compounds of the present invention, or a stereoisomer or pharmaceutically acceptable salt from thereof, are those in which:

X is O;

W is a —NR$_2$R$_3$ or a 3- to 12-membered nitrogen containing ring, wherein the ring is (i) attached through the nitrogen atom, (ii) may optionally contain 1-4 heteroatoms selected, from N, O, and S and (iii) be optionally substituted with one or more $R_{10a}$'s;

m is 1-2;

n is 1-2;

$R_1$ is H or alkyl;

$R_2$ is H, alkyl or cycloalkyl, wherein the cycloalkyl may be optionally substituted with may be optionally substituted with be optionally substituted with one or more $R_{9a}$'s;

$R_3$ is H, alkyl or cycloalkyl, wherein the cycloalkyl may be optionally substituted with may be optionally substituted with be optionally substituted with one or more $R_{9a}$'s;

$R_6$, at each occurrence, is independently selected from halo, alkyl, haloalkyl, haloalkoxy, and aryl optionally substituted with halo;

$R_{9a}$, at each occurrence, is independently selected from alkyl, haloalkyl, aryl, cycloalkyl, heteroaryl, heterocyclyl, halo, —CN, —NO$_2$, —C(=O)OR$_{14}$, —OCF$_3$, —OR$_{14}$, or arylalkyl;

$R_{10a}$, at each occurrence, is independently selected from alkyl, haloalkyl, aryl, cycloalkyl, heteroaryl, heterocyclyl, halo, —CN, —NO$_2$, —C(=O)OR$_{14}$, —OCF$_3$, —OR$_{14}$, or arylalkyl, wherein the aryl, cycloalkyl, heteroaryl, and heterocyclyl may be optionally substituted with on or more $R_{14a}$'s;

$R_{14}$, at each occurrence, is independently selected from hydrogen, alkyl, cycloalkyl, aryl or heteroaryl, wherein the alkyl, cycloalkyl, aryl and heteroaryl may be optionally substituted with be optionally substituted with 0-3 $R_{14a}$;

$R_{14a}$, at each occurrence, is independently selected from alkyl, haloalkyl, aryl, cycloalkyl, heteroaryl, heterocyclyl, halo, —CN, —NO$_2$, —C(=O)OR$_{24}$, —OCF$_3$, —OR$_{24}$ or arylalkyl; and $R_{24}$, at each occurrence, is independently selected from hydrogen, alkyl, cycloalkyl, aryl or heteroaryl.

In yet another embodiment, compounds of the present invention, or a stereoisomer or pharmaceutically acceptable salt from thereof, are those in which:

X is O;

W is a 3- to 12-membered nitrogen containing ring, wherein the ring is (i) attached through the nitrogen atom, (ii) may optionally contain 1-4 heteroatoms selected from N, O, and S and (iii) be optionally substituted with one or more $R_{10a}$'s;

m is 1-2;

n is 1-2;

$R_1$ is H or alkyl;

$R_6$, at each occurrence, is independently selected from halo, alkyl, haloalkyl, haloalkoxy, and aryl optionally substituted with halo;

$R_{10a}$, at each occurrence, is independently selected from alkyl, haloalkyl, aryl, cycloalkyl, heteroaryl, heterocyclyl, halo, —CN, —NO$_2$, —C(=O)OR$_{14}$, —OCF$_3$, —OR$_{14}$, or arylalkyl, wherein the aryl, cycloalkyl, heteroaryl, heterocyclyl may be optionally substituted with on or more $R_{14a}$'s;

$R_{14}$, at each occurrence, is independently selected from hydrogen, alkyl, cycloalkyl, aryl or heteroaryl, wherein the alkyl, cycloalkyl, aryl and heteroaryl may be optionally substituted with be optionally substituted with 0-3 $R_{14a}$;

$R_{14a}$, at each occurrence, is independently selected from alkyl, haloalkyl, aryl, cycloalkyl, heteroaryl, heterocyclyl, halo, —CN, —NO$_2$, —C(=O)OR$_{24}$, —OCF$_3$, —OR$_{24}$ or arylalkyl; and $R_{24}$, at each occurrence, is independently selected from hydrogen, alkyl, cycloalkyl, aryl or heteroaryl.

In still yet another embodiment, compounds of the present invention, or a stereoisomer or pharmaceutically acceptable salt from thereof, are those in which:

X is O;

W is a 5- to 12-membered nitrogen containing ring, wherein the ring is (i) attached through the nitrogen atom, (ii) may optionally contain 1-4 heteroatoms selected from N, O, and S and (iii) be optionally substituted with one or more $R_{10a}$'s;

is 1-2;

n is 1-2;

$R_1$ is H or alkyl;

$R_6$, at each occurrence, is independently selected from halo, alkyl, haloalkyl, haloalkoxy, and aryl optionally substituted with halo;

$R_{10a}$, at each occurrence, is independently selected from alkyl, haloalkyl, aryl, cycloalkyl, heteroaryl, halo, —CN, —NO$_2$, —C(=O)OR$_{14}$, —OCF$_3$, —OR$_{14}$, or arylalkyl, wherein the aryl, cycloalkyl and heteroaryl may be optionally substituted with on or more $R_{14a}$'s;

$R_{14}$, at each occurrence, is independently selected from hydrogen, alkyl, cycloalkyl, aryl or heteroaryl, wherein the alkyl, cycloalkyl, aryl and heteroaryl may be optionally substituted with be optionally substituted with 0-3 $R_{14a}$;

$R_{14a}$, at each occurrence, is independently selected from alkyl, haloalkyl, aryl, cycloalkyl, heteroaryl, halo, —CN, —NO$_2$, —C(=O)OR$_{24}$, —OCF$_3$, —OR$_{24}$ or arylalkyl; and $R_{24}$, at each occurrence, is independently selected from hydrogen, alkyl, cycloalkyl, aryl or heteroaryl.

In one embodiment, compounds of the present invention, or a stereoisomer or pharmaceutically acceptable salt from thereof, are those in which:

X is O;

W is a 5- or 6-membered nitrogen containing ring, wherein the ring is (i) attached through the nitrogen atom, (ii) may optionally contain 1-3 heteroatoms selected from N, O, and S and (iii) be optionally substituted with one or more $R_{10a}$'s;

m is 2;

n is 1-2;

$R_1$ is H or alkyl;

$R_6$, at each occurrence, is independently selected from halo, alkyl, haloalkyl, haloalkoxy, and aryl optionally substituted with halo;

$R_{10a}$, at each occurrence, is independently selected from alkyl, haloalkyl, aryl, cycloalkyl, heteroaryl, halo, —C(=O)OR$_{14}$, —OCF$_3$, —OR$_{14}$ or arylalkyl, wherein the aryl, cycloalkyl and heteroaryl may be optionally substituted with on or more $R_{14a}$'s;

$R_{14}$, at each occurrence, is independently selected from hydrogen, alkyl, cycloalkyl or aryl, wherein the alkyl, cycloalkyl and aryl may be optionally substituted with be optionally substituted with 0-3 $R_{14a}$;

$R_{14a}$, at each occurrence, is independently selected from alkyl, haloalkyl, aryl, cycloalkyl, heteroaryl, halo, —C(=O)OR$_{24}$, —OCF$_3$, —OR$^{24}$ or arylalkyl; and $R_{24}$, at each occurrence, is independently selected from hydrogen, alkyl, cycloalkyl, or aryl.

In still yet another embodiment, compounds of the present invention, or a stereoisomer or pharmaceutically acceptable salt from thereof, are those in which:

X is O;

W is pyrrolidinyl, piperazinyl or piperidinyl, wherein the ring is (i) attached through a nitrogen atom and may be optionally substituted with one or more $R_{10a}$'s;

m is 2;

n is 1-2;

$R_1$ is H or isopropyl;

$R_6$, at each occurrence, is independently selected from Cl, Br, F, t-butyl, —CF$_3$, —CF$_2$ CF$_3$, —OCF$_3$, and phenyl optionally substituted with Cl, Br, F or I;

$R_{10a}$, at each occurrence, is independently selected from methyl, —CF$_3$, —CF$_2$ CF$_3$, aryl, Cl, F, Br, —C(=O)OH, —OCF$_3$, —OH or benzyl.

In one embodiment, compounds of Formula (I), or a stereoisomer or pharmaceutically acceptable salt from thereof, are those compounds exemplified in the examples.

In another embodiment, the present invention is directed to a pharmaceutical composition, comprising a pharmaceutically acceptable carrier and a therapeutically effective amount of a compound of the present invention.

In another embodiment, the present invention is directed to a method for modulation of chemokine or chemokine receptor activity comprising administering to a patient in need thereof a therapeutically effective amount of a compound of the present invention.

In another embodiment, the present invention is directed to a method for modulation of CCR-2 receptor activity comprising administering to a patient in need thereof a therapeutically effective amount of a compound of the present invention.

In another embodiment, the present invention is directed to a method for modulation of MCP-1 activity that is mediated by the CCR-2 receptor comprising administering to a patient in need thereof a therapeutically effective amount of a compound of the present invention.

In another embodiment, the present invention is directed to a method for treating disorders, comprising administering to a patient in need thereof a therapeutically effective amount of a compound of the present invention, said wherein said disorder is selected from osteoarthritis, aneurysm, fever, cardiovascular effects, Crohn's disease, congestive heart failure, autoimmune diseases, HIV-infection, HIV-associated dementia, psoriasis, idiopathic pulmonary fibrosis, transplant arteriosclerosis, physically- or chemically-induced brain trauma, inflammatory bowel disease, alveolitis, colitis, systemic lupus erythematosus, nephrotoxic serum nephritis, glomerularnephritis, asthma, multiple sclerosis, atherosclerosis, rheumatoid arthritis, restinosis, organ transplantation, psoriatic arthritis, multiple myeloma, allergies, for example, skin and mast cell degranulation in eye conjunctiva, hepatocellular carcinoma, osteoporosis, renal fibrosis and cancer, preferably, Crohn's disease, psoriasis, inflammatory bowel disease, systemic lupus erythematosus, multiple sclerosis, rheumatoid arthritis, multiple myeloma, allergies, for example, skin and mast cell degranulation in eye conjunctiva, hepatocellular carcinoma, osteoporosis and renal fibrosis.

In another embodiment, the present invention is directed to a method for treating inflammatory diseases, comprising administering to a patient in need thereof a therapeutically effective amount of a compound of the present invention.

In another embodiment, the present invention is directed to a method for treating inflammatory bowel disease, comprising administering to a patient in need thereof a therapeutically effective amount of a compound of the present invention.

In another embodiment, the present invention is directed to a method for treating Crohn's disease, comprising administering to a patient in need thereof a therapeutically effective amount of a compound of the present invention.

In another embodiment, the present invention is directed to a method for treating psoriasis, comprising administering to a patient in need thereof a therapeutically effective amount of a compound of the present invention.

In another embodiment, the present invention is directed to a method for treating systemic lupus erythematosus, comprising administering to a patient in need thereof a therapeutically effective amount of a compound of the present invention.

In another embodiment, the present invention is directed to a method for treating multiple sclerosis, comprising administering to a patient in need thereof a therapeutically effective amount of a compound of the present invention.

In another embodiment, the present invention is directed to a method for treating rheumatoid arthritis, comprising administering to a patient in need thereof a therapeutically effective amount of a compound of the present invention.

In another embodiment, the present invention is directed to a method for treating psoriatic arthritis, comprising administering to a patient in need thereof a therapeutically effective amount of a compound of the present invention.

In another embodiment, the present invention is directed to a method for treating multiple myeloma, comprising administering to a patient in need thereof a therapeutically effective amount of a compound of the present invention.

In another embodiment, the present invention is directed to a method for treating allergies, for example, skin and mast cell degranulation in eye conjunctiva, comprising administering to a patient in need thereof a therapeutically effective amount of a compound of the present invention.

In another embodiment, the present invention is directed to a method for treating hepatocellular carcinoma, comprising administering to a patient in need thereof a therapeutically effective amount of a compound of the present invention.

In another embodiment, the present invention is directed to a method for treating osteoporosis, comprising administering to a patient in need thereof a therapeutically effective amount of a compound of the present invention.

In another embodiment, the present invention is directed to a method for treating renal fibrosis, comprising administering to a patient in need thereof a therapeutically effective amount of a compound of the present invention.

In another embodiment, the present invention is directed to a method for treating inflammatory diseases, for example, inflammatory diseases which are at least partially mediated by CCR-2, comprising administering to a patient in need thereof a therapeutically effective amount of a compound of the present invention.

In another embodiment, the present invention is directed to a method for modulation of CCR2 activity comprising administering to a patient in need thereof a therapeutically effective amount of a compound of the present invention.

In another embodiment, the present invention is directed the use of a compound of the present invention in the preparation of a medicament for the treatment of a disorder, said disorder is selected from osteoarthritis, aneurysm, fever, cardiovascular effects, Crohn's disease, congestive heart failure, autoimmune diseases, HIV-infection, HIV-associated dementia, psoriasis, idiopathic pulmonary fibrosis, transplant arteriosclerosis, physically- or chemically-induced brain trauma, inflammatory bowel disease, alveolitis, colitis, systemic lupus erythematosus, nephrotoxic serum nephritis, glomerularnephritis, asthma, multiple sclerosis, atherosclerosis, rheumatoid arthritis, restinosis, organ transplantation, psoriatic arthritis, multiple myeloma, allergies, for example, skin and mast cell degranulation in eye conjunctiva, hepatocellular carcinoma, osteoporosis, renal fibrosis and cancer, preferably, Crohn's disease, psoriasis, inflammatory bowel disease, systemic lupus erythematosus, multiple sclerosis, rheumatoid arthritis, multiple myeloma, allergies, for example, skin and mast cell degranulation in eye conjunctiva, hepatocellular carcinoma, osteoporosis and renal fibrosis.

In another embodiment, the present invention is directed to a compound of the present invention for use in therapy.

In another embodiment, the present invention is directed to a pharmaceutical composition comprising a compound of the present invention and one or more active ingredients.

In another embodiment, the present invention is directed to a method for modulation of chemokine or chemokine receptor activity comprising administering to a patient in need thereof a therapeutically effective amount of a pharmaceutical composition comprised of a compound of the present invention and one or more active ingredients.

In another embodiment, the present invention is directed to a method for modulation of CCR-2 receptor activity comprising administering to a patient in need thereof a therapeutically effective amount of a pharmaceutical composition comprised of a compound of the present invention and one or more active ingredients.

In yet another embodiment, the present invention is directed to a method for modulation of MCP-1 activity that is mediated by the CCR-2 receptor comprising administering to a patient in need thereof a therapeutically effective amount of a pharmaceutical composition comprised of a compound of the present invention and one or more active ingredients.

In another embodiment, the present invention is directed to a method for treating a disorder, comprising administering to a patient in need thereof a therapeutically effective amount of a pharmaceutical composition comprised of a compound of the present invention and one or more active ingredients, wherein said disorder is selected from osteoarthritis, aneurysm, fever, cardiovascular effects, Crohn's disease, congestive heart failure, autoimmune diseases, HIV-infection, HIV-associated dementia, psoriasis, idiopathic pulmonary fibrosis, transplant arteriosclerosis, physically- or chemically-induced brain trauma, inflammatory bowel disease, alveolitis, colitis, systemic lupus erythematosus, nephrotoxic serum nephritis, glomerularnephritis, asthma, multiple sclerosis, atherosclerosis, rheumatoid arthritis, restinosis, organ transplantation, psoriatic arthritis, multiple myeloma, allergies, for example, skin and mast cell degranulation in eye conjunctiva, hepatocellular carcinoma, osteoporosis, renal fibrosis and cancer, preferably, Crohn's disease, psoriasis, inflammatory bowel disease, systemic lupus erythematosus, multiple sclerosis, rheumatoid arthritis, multiple myeloma, allergies, for example, skin and mast cell degranulation in eye conjunctiva, hepatocellular carcinoma, osteoporosis and renal fibrosis.

In yet another embodiment, the present invention, is directed to a method for treating inflammatory diseases, preferably, inflammatory diseases which are at least partially mediated by CCR-2, comprising administering to a patient in need thereof a therapeutically effective amount of a pharmaceutical composition comprised of a compound of present invention and one or more active ingredients.

In another embodiment, the present invention is directed to a method for modulation of CCR-2 activity comprising administering to a patient in need thereof a therapeutically effective amount of a pharmaceutical composition comprised of a compound of the present invention and one or more active ingredients.

In another embodiment, the present invention is directed to the use of a pharmaceutical composition comprised of a compound of the present invention and one or more active ingredients in the preparation of a medicament for the treatment of a disorder, said disorder is selected from osteoarthritis, aneurysm, fever, cardiovascular effects, Crohn's disease, congestive heart failure, autoimmune diseases, IV-infection, HIV-associated dementia, psoriasis, idiopathic pulmonary fibrosis, transplant arteriosclerosis, physically- or chemically-induced brain trauma, inflammatory bowel disease, alveolitis, colitis, systemic lupus erythematosus, nephrotoxic serum nephritis, glomerularnephritis, asthma, multiple sclerosis, atherosclerosis, rheumatoid arthritis, restinosis, organ transplantation, psoriatic arthritis, multiple myeloma, allergies, for example, skin and mast cell degranulation in eye conjunctiva, hepatocellular carcinoma, osteoporosis, renal fibrosis and cancer, preferably, Crohn's disease, psoriasis, inflammatory bowel disease, systemic lupus erythematosus, multiple sclerosis, rheumatoid arthritis, multiple myeloma, allergies, for example, skin and mast cell degranulation in eye conjunctiva, hepatocellular carcinoma, osteoporosis and renal fibrosis.

In still yet another embodiment, the present invention is directed to the use of a pharmaceutical composition comprised of a compound of the present invention and one or more active ingredients in therapy.

In another embodiment, the present invention provides a compound of the present invention for use in therapy for treating an inflammatory disease.

In another embodiment, the present invention provides a combined preparation of a compound of the present invention and additional therapeutic agent(s) for simultaneous, separate or sequential use in therapy.

In another embodiment, the present invention provides a combined preparation of a compound of the present invention and additional therapeutic agent(s) for simultaneous, separate or sequential use in treatment of an inflammatory disease.

In another embodiment, the present invention provides a novel article of manufacture, comprising: (a) a first container; (b) a pharmaceutical composition located within the first container, wherein the composition, comprises: a first therapeutic agent, comprising: a compound of the present invention; and (c) a package insert stating that the pharmaceutical composition can be used for the treatment of an inflammatory disease.

In another preferred embodiment, the present invention provides a novel article of manufacture, further comprising: (d) a second container; wherein components (a) and (b) are located within the second container and component (c) is located within or outside of the second container.

In another embodiment, the present invention provides a novel article of manufacture, comprising: (a) a first container; (b) a pharmaceutical composition located within the first container, wherein the composition, comprises: a first therapeutic agent, comprising: a compound of the present invention; and (c) a package insert stating that the pharmaceutical composition can be used in combination with a second therapeutic agent to treat an inflammatory disease.

The invention may be embodied in other specific forms without departing from the spirit or essential attributes thereof. This invention also encompasses all combinations of alternative aspects of the invention noted herein. It is understood that any and all embodiments of the present invention may be taken in conjunction with any other embodiment to describe additional embodiments of the present invention. Furthermore, any elements of an embodiment may be combined with any and all other elements from any of the embodiments to describe additional embodiments.

Definitions

The compounds herein described may have asymmetric centers. Compounds of the present invention containing an asymmetrically substituted atom may be isolated in optically active or racemic forms. It is well known in the art how to prepare optically active forms, such as by resolution of racemic forms or by synthesis from optically active starting materials. Many geometric isomers of olefins, C=N double bonds, and the like can also be present in the compounds described herein, and all such stable isomers are contemplated in the present invention. Cis and trans geometric isomers of the compounds of the present invention are described and may be isolated as a mixture of isomers or as separated isomeric forms. All chiral, diastereomeric, racemic forms and all geometric isomeric forms of a structure are intended, unless the specific stereochemistry or isomeric form is specifically indicated.

One enantiomer of a compound of Formula I may display superior activity compared with the other. Thus, all of the stereochemistries are considered to be a part of the present invention. When required, separation of the racemic material can be achieved by HPLC using a chiral column or by a resolution using a resolving agent such as camphonic chloride as in Young, S. D. et al., *Antimicrobial Agents and Chemotherapy* 1995, 2602-2605.

The term "substituted," as used herein, means that any one or more hydrogens on the designated atom or ring is replaced with a selection from the indicated group, provided that the designated atom's or ring atom's normal valency is not exceeded, and that the substitution results in a stable compound. When a substituent is keto (i.e., =O), then 2 hydrogens on the atom are replaced.

When any variable (e.g., $R_4$) occurs more than one time in any constituent or formula for a compound, its definition at each occurrence is independent of its definition at every other occurrence. Thus, for example, if a group is shown to be substituted with $(R_4)_m$ and m is 0-3, then said group may optionally be substituted with up to three $R_4$ groups and $R_4$ at each occurrence is selected independently from the definition of $R_4$. Also, combinations of substituents and/or variables are permissible only if such combinations result in stable compounds.

When a bond to a substituent is shown to cross a bond connecting two atoms in a ring, then such substituent may be bonded to any atom on the ring. When a substituent is listed without indicating the atom via which such substituent is bonded to the rest of the compound of a given formula, then such substituent may be bonded via any atom in such substituent. Combinations of substituents and/or variables are permissible only if such combinations result in stable compounds.

As used herein, "alkyl" is intended to include both branched and straight-chain saturated aliphatic hydrocarbon groups containing 1 to 20 carbons, preferably 1 to 10 carbons, more preferably 1 to 8 carbons, in the normal chain, such as methyl, ethyl, propyl, isopropyl, butyl, t-butyl, isobutyl, pentyl, hexyl, isohexyl, heptyl, 4,4-dimethylpentyl, octyl, 2,2,4-trimethyl-pentyl, nonyl, decyl, undecyl, dodecyl, the various branched chain isomers thereof, and the like as well as such groups may optionally include 1 to 4 substituents such as halo, for example F, Br, Cl, or I, or $CF_3$, alkyl, alkoxy, aryl, aryloxy, aryl(aryl) or diaryl, arylalkyl, arylalkyloxy, alkenyl, cycloalkyl, cycloalkylalkyl, cycloalkylalkyloxy, amino, hydroxy, hydroxyalkyl, acyl, heteroaryl, heteroaryloxy, heteroarylalkyl, heteroarylalkoxy, aryloxyalkyl, alkylthio, arylalkylthio, aryloxyaryl, alkylamido, alkanoylamino, arylcarbonylamino, nitro, cyano, thiol, haloalkyl, trihaloalkyl, and/or alkylthio.

Unless otherwise indicated, the term "alkenyl" as used herein by itself or as part of another group refers to straight or branched chain radicals of 2 to 20 carbons, preferably 2 to 12 carbons, and more preferably 1 to 8 carbons in the normal chain, which include one to six double bonds in the normal chain, such as vinyl, 2-propenyl, 3-butenyl, 2-butenyl, 4-pentenyl, 3-pentenyl, 2-hexenyl, 3-hexenyl, 2-heptenyl, 3-heptenyl, 4-heptenyl, 3-octenyl, 3-nonenyl, 4-decenyl, 3-undecenyl, 4-dodecenyl, 4,8,12-tetradecatrienyl, and the like, and which may be optionally substituted with 1 to 4 substituents, namely, halogen, haloalkyl, alkyl, alkoxy, alkenyl, alkynyl, aryl, arylalkyl, cycloalkyl, amino, hydroxy, heteroaryl, cycloheteroalkyl, alkanoylamino, alkylamido, arylcarbonylamino, nitro, cyano, thiol, alkylthio, and/or any of the alkyl substituents set out herein.

Unless otherwise indicated, the term "alkynyl" as used herein by itself or as part of another group refers to straight or branched chain radicals of 2 to 20 carbons, preferably 2 to 12 carbons and more preferably 2 to 8 carbons in the normal chain, which include one triple bond in the normal chain, such as 2-propynyl, 3-butynyl, 2-butynyl, 4-pentynyl, 3-pentynyl, 2-hexynyl, 3-hexynyl, 2-heptynyl, 3-heptynyl, 4-heptynyl, 3-octynyl, 3-nonynyl, 4-decynyl, 3-undecynyl, 4-dodecynyl, and the like, and which may be optionally substituted with 1 to 4 substituents, namely, halogen, haloalkyl, alkyl, alkoxy, alkenyl, alkynyl, aryl, arylalkyl, cycloalkyl, amino, heteroaryl, cycloheteroalkyl, hydroxy, alkanoylamino, alkylamido, arylcarbonylamino, nitro, cyano, thiol, and/or alkylthio, and/or any of the alkyl substituents set out herein.

Unless otherwise indicated, the term "cycloalkyl" as employed herein alone or as part of another group includes saturated or partially unsaturated (containing 1 or 2 double bonds) cyclic hydrocarbon groups containing 1 to 3 rings, including monocyclic alkyl, bicyclic alkyl (or bicycloalkyl) and tricyclic alkyl, containing a total of 3 to 20 carbons forming the ring, preferably 3 to 10 carbons, forming the ring and which may be fused to 1 or 2 aromatic rings as described for aryl, which includes cyclopropyl, cyclobutyl, cyclopentyl, cyclohexyl, cycloheptyl, cyclooctyl, cyclodecyl and cyclododecyl, cyclohexenyl,

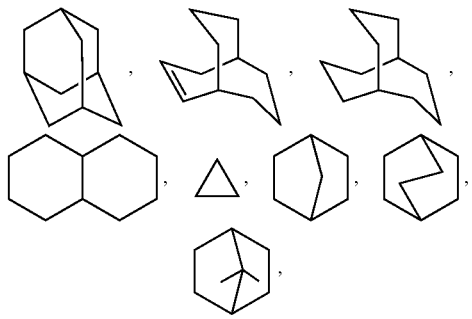

any of which groups may be optionally substituted with 1 to 4 substituents such as halogen, alkyl, alkoxy, hydroxy, aryl, aryloxy, arylalkyl, cycloalkyl, alkylamido, alkanoylamino, oxo, acyl, arylcarbonylamino, amino, nitro, cyano, thiol, and/or alkylthio, and/or any of the substituents for alkyl.

Where alkyl groups as defined above have single bonds for attachment to other groups at two different carbon atoms, they are termed "alkylene" groups and may optionally be substituted as defined above for "alkyl".

Where alkenyl groups as defined above and alkynyl groups as defined above, respectively, have single bonds for attachment at two different carbon atoms, they are termed "alkenylene groups" and "alkynylene groups", respectively, and may optionally be substituted as defined above for "alkenyl" and "alkynyl".

"Halo" or "halogen" as used herein refers to fluoro, chloro, bromo, and iodo; and "haloalkyl" is intended to include both branched and straight-chain saturated aliphatic hydrocarbon groups, for example $CF_3$, having the specified number of carbon atoms, substituted with 1 or more halogen (for example $-C_vF_w$ where v=1 to 3 and w=1 to (2v+1)).

Unless otherwise indicated, the term "aryl" as employed herein alone or as part of another group refers to monocyclic and bicyclic aromatic groups containing 6 to 10 carbons in the ring portion (such as phenyl or -naphthyl, including 1-naphthyl and 2-naphthyl) and may optionally include 1 to 3 additional rings fused to a carbocyclic ring or a heterocyclic ring (such as aryl, cycloalkyl, heteroaryl, or cycloheteroalkyl rings, for example:

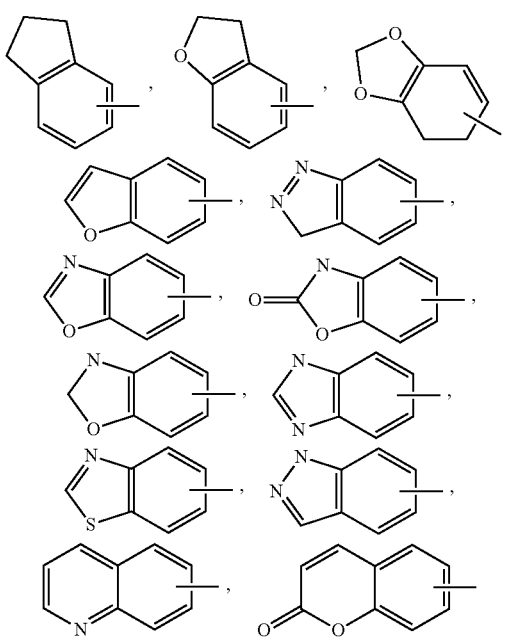

and may be optionally substituted through available carbon atoms with 1, 2, or 3 substituents, for example, hydrogen, halo, haloalkyl, alkyl, haloalkyl, alkoxy, haloalkoxy, alkenyl, trifluoromethyl, trifluoromethoxy, alkynyl, cycloalkyl-alkyl, cycloheteroalkyl, cycloheteroalkylalkyl, aryl, heteroaryl, arylalkyl, aryloxy, aryloxyalkyl, arylalkoxy, arylthio, arylazo, heteroarylalkyl, heteroarylalkenyl, heteroarylheteroaryl, heteroaryloxy, hydroxy, nitro, cyano, amino, substituted amino wherein the amino includes 1 or 2 substituents (which are alkyl, aryl, or any of the other aryl compounds mentioned in the definitions), thiol, alkylthio, arylthio, heteroarylthio, arylthioalkyl, alkoxyarylthio, alkylcarbonyl, arylcarbonyl, alkyl-aminocarbonyl, arylaminocarbonyl, alkoxycarbonyl, aminocarbonyl, alkylcarbonyloxy, arylcarbonyloxy, alkylcarbonylamino, arylcarbonylamino, arylsulfinyl, arylsulfinylalkyl, arylsulfonylamino, or arylsulfonaminocarbonyl, and/or any of the alkyl substituents set out herein.

Unless otherwise indicated, the term "lower alkoxy", "alkoxy", "aryloxy" or "aralkoxy" as employed herein alone or as part of another group includes any of the above alkyl, aralkyl, or aryl groups linked to an oxygen atom.

Unless otherwise indicated, the term "amino" as employed herein alone or as part of another group refers to amino that may be substituted with one or two substituents, which may be the same or different, such as alkyl, aryl, arylalkyl, heteroaryl, heteroarylalkyl, cycloheteroalkyl, cycloheteroalkylalkyl, cycloalkyl, cycloalkylalkyl, haloalkyl, hydroxyalkyl, alkoxyalkyl, or thioalkyl. These substituents may be further substituted with a carboxylic acid and/or any of the $R^1$ groups or substituents for $R^1$ as set out above. In addition, the amino substituents may be taken together with the nitrogen atom to which they are attached to form 1-pyrrolidinyl, 1-piperidinyl, 1-azepinyl, 4-morpholinyl, 4-thiamorpholinyl, 1-piperazinyl, 4-alkyl-1-piperazinyl, 4-arylalkyl-1-piperazinyl, or 4-diarylalkyl-1-piperazinyl, all of which may be optionally substituted with alkyl, alkoxy, alkylthio, halo, trifluoromethyl, or hydroxy.

Unless otherwise indicated, the term "lower alkylthio," "alkylthio," "arylthio," or "aralkylthio" as employed herein alone or as part of another group includes any of the above alkyl, aralkyl, or aryl groups linked to a sulfur atom.

Unless otherwise indicated, the term "lower alkylamino," "alkylamino," "arylamino," or "arylalkylamino" as employed herein alone or as part of another group includes any of the above alkyl, aryl, or arylalkyl groups linked to a nitrogen atom.

As used herein, the term "heterocyclyl" or "heterocyclic system" is intended to mean a stable 5, 6, or 7-membered monocyclic or bicyclic or 7, 8, 9, or 10-membered bicyclic heterocyclic ring which is saturated, partially unsaturated or unsaturated (aromatic), and which consists of carbon atoms and 1, 2, 3, or 4 heteroatoms independently selected from the group consisting of N, NH, O and S and including any bicyclic group in which any of the above-defined heterocyclic rings is fused to a benzene ring. The nitrogen and sulfur heteroatoms may optionally be oxidized. The heterocyclic ring may be attached to its pendant group at any heteroatom or carbon atom, which results in a stable structure. The heterocyclic rings described herein may be substituted on carbon or on a nitrogen atom if the resulting compound is stable. If specifically noted, a nitrogen in the heterocycle may optionally be quaternized. It is preferred that when the total number of S and O atoms in the heterocycle exceeds 1, then these heteroatoms are not adjacent to one another. As used herein, the term "aromatic heterocyclic system" or "heteroaryl" is intended to mean a stable 5- to 7-membered monocyclic or bicyclic or 7- to 10-membered bicyclic heterocyclic aromatic ring which consists of carbon atoms and from 1 to 4 heteroatoms independently selected from the group consisting of N, O and S and is aromatic in nature.

Examples of heterocycles include, but are not limited to, 1H-indazole, 2-pyrrolidonyl, 2H,6H-1,5,2-dithiazinyl, 2H-pyrrolyl, 1H-indolyl, 4-piperidonyl, 4aH-carbazole, 4H-quinolizinyl, 6H-1,2,5-thiadiazinyl, acridinyl, azocinyl, benzimidazolyl, benzofuranyl, benzothiofuranyl, benzothiophenyl, benzoxazolyl, benzthiazolyl, benztriazolyl, benztetrazolyl, benzisoxazolyl, benzisothiazolyl, benzimidazalonyl, carbazolyl, 4aH-carbazolyl, β-carbolinyl, chromanyl, chromenyl, cinnolinyl, decahydroquinolinyl, 2H,6H-1,5,2-dithiazinyl, dihydrofuro[2,3-b]tetrahydrofuran, furanyl, furazanyl, imidazolidinyl, imidazolinyl, imidazolyl, indazolyl, indolenyl, indolinyl, indolizinyl, indolyl, isobenzofuranyl, isochromanyl, isoindazolyl, isoindolinyl, isoindolyl, isoquinolinyl, benzimidazolyl, isothiazolyl, isoxazolyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxazolidinylperimidinyl, phenanthridinyl, phenanthrolinyl, phenarsazinyl, phenazinyl, phenothiazinyl, phenoxathiinyl, phenoxazinyl, phthalazinyl, piperazinyl, piperidinyl, pteridinyl, piperidonyl, 4-piperidonyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, pyrrolyl, quinazolinyl, quinolinyl, 4H-quinolizinyl, quinoxalinyl, quinuclidinyl, carbolinyl, tetrahydrofuranyl, tetrahydroisoquinolinyl, tetrahydroquinolinyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl, triazinyl, 1,2,3-triazolyl 1,2,4-triazolyl, 1,2,5-triazolyl, 1,3,4-triazolyl, tetrazolyl, and xanthenyl. In another aspect of the invention, the heterocycles include, but are not limited to, pyridinyl, thiophenyl, furanyl, indazolyl, benzothiazolyl, benzimidazolyl, benzothiaphenyl, benzofuranyl, benzoxazolyl, benzisoxazolyl, quinolinyl, isoquinolinyl, imidazolyl, indolyl, isoidolyl, piperidinyl, piperidonyl, 4-piperidonyl, piperonyl, pyrrazolyl, 1,2,4-triazolyl, 1,2,3-triazolyl, tetrazolyl, thiazolyl, oxazolyl, pyrazinyl, and pyrimidinyl. Also included are fused ring and spiro compounds containing, for example, the above heterocycles.

Examples of heteroaryls are 1H-indazole, 2H,6H-1,5,2-dithiazinyl, indolyl, 4aH-carbazole, 4H-quinolizinyl, 6H-1,2,5-thiadiazinyl, acridinyl, azocinyl, benzimidazolyl, benzofuranyl, benzothiofuranyl, benzothiophenyl, benzoxazolyl, benzthiazolyl, benztriazolyl, benztetrazolyl, benzisoxazolyl, benzisothiazolyl, benzimidazalonyl, carbazolyl, 4aH-carbazolyl, 3-carbolinyl, chromanyl, chromenyl, cinnolinyl, decahydroquinolinyl, 2H,6H-1,5,2-dithiazinyl, dihydrofuro[2,3-b]tetrahydrofuran, furanyl, furazanyl, imidazolidinyl, imidazolinyl, imidazolyl, indazolyl, indolenyl, indolinyl, indolizinyl, indolyl, isobenzofuranyl, isochromanyl, isoindazolyl, isoindolinyl, isoindolyl, isoquinolinyl(benzimidazolyl), isothiazolyl, isoxazolyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxazolidinylperimidinyl, phenanthridinyl, phenanthrolinyl, phenarsazinyl, phenazinyl, phenothiazinyl, phenoxathiinyl, phenoxazinyl, phthalazinyl, piperazinyl, piperidinyl, pteridinyl, piperidonyl, 4-piperidonyl, pteridinyl, purinyl, pyranyl, pyrazinyl, pyrazolidinyl, pyrazolinyl, pyrazolyl, pyrazolotriazinyl, pyridazinyl, pyridooxazole, pyridoimidazole, pyridothiazole, pyridinyl, pyridyl, pyrimidinyl, pyrrolidinyl, pyrrolinyl, pyrrolyl, quinazolinyl, quinolinyl, 4H-quinolizinyl, quinoxalinyl, quinuclidinyl, carbolinyl, tetrahydrofuranyl, tetrahydroisoquinolinyl, tetrahydroquinolinyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl, triazinyl, 1,2,3-triazolyl, 1,2,4-triazolyl, 1,2,5-triazolyl, 1,3,4-triazolyl, tetrazolyl, and xanthenyl. In another aspect of the invention, examples of heteroaryls are indolyl, benzimidazolyl, benzofuranyl, benzothiofuranyl, benzoxazolyl, benzthiazolyl, benztriazolyl, benztetrazolyl, benzisoxazolyl, benzisothiazolyl, benzimidazalonyl, cinnolinyl, furanyl, imidazolyl, indazolyl, indolyl, isoquinolinyl isothiazolyl, isoxazolyl, oxazolyl, pyrazinyl, pyrazolyl, pyrazolotriazinyl, pyridazinyl, pyridyl, pyridinyl, pyrimidinyl, pyrrolyl, quinazolinyl, quinolinyl, thiazolyl, thienyl, and tetrazolyl.

The term "heterocyclylalkyl" or "heterocyclyl" as used herein alone or as part of another group refers to heterocyclyl groups as defined above linked through a C atom or heteroatom to an alkyl chain.

The term "heteroarylalkyl" or "heteroarylalkenyl" as used herein alone or as part of another group refers to a heteroaryl group as defined above linked through a C atom or heteroatom to an alkyl chain, alkylene, or alkenylene as defined above.

The term "cyano" as used herein, refers to a —CN group.
The term "nitro" as used herein, refers to an —NO$_2$ group.
The term "hydroxy" as used herein, refers to an OH group.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used herein, "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic residues such as amines; alkali or organic salts of acidic residues such as carboxylic acids; and the like. The pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, palmidic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, isethionic, and the like.

The pharmaceutically acceptable salts of the present invention can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, non-aqueous media like ether, ethyl acetate, ethanol, isopropanol, or acetonitrile are preferred. Lists of suitable salts are found in *Remington's Pharmaceutical Sciences*, 17th ed., p. 1418 (Mack Publishing Company, Easton, Pa., 1985), the disclosure of which is hereby incorporated by reference.

Any compound that can be converted in vivo to provide the bioactive agent (i.e., the compound of formula I) is a prodrug within the scope and spirit of the invention.

The term "prodrugs" as employed herein includes esters, carbamates and carbonates formed by reacting one or more hydroxyls of compounds of formula I with alkyl, alkoxy, or aryl substituted acylating agents employing procedures known to those skilled in the art to generate acetates, pivalates, methylcarbonates, benzoates, and the like.

Various forms of prodrugs are well known in the art and are described in:

a) Wermuth, C. G. et al., *The Practice of Medicinal Chemistry*, Ch. 31 (Academic Press, 1996);
Bundgaard, H., ed., *Design of Prodrugs* (Elsevier, 1985);
c) Krause, B. R. et al., Chapter 6: "ACAT Inhibitors: Physiologic Mechanisms for Hypolipidemic and Anti-Atherosclerotic Activities in Experimental Animals", *Inflammation: Mediators and Pathways*, Ruffolo, Jr., R. R. et al., eds., pp. 173-198 (CRC Press, Inc., 1995); and
d) Testa, B. et al., *Hydrolysis in Drug and Prodrug Metabolism* (Wiley-VCH, 2003).

Said references are incorporated herein by reference.

In addition, compounds of the formula I are, subsequent to their preparation, preferably isolated and purified to obtain a composition containing an amount by weight equal to or greater than 99% formula I compound ("substantially pure" compound I), which is then used or formulated as described herein. Such "substantially pure" compounds of the formula I are also contemplated herein as part of the present invention.

All stereoisomers of the compounds of the instant invention are contemplated, either in admixture or in pure or substantially pure form. The compounds of the present invention can have asymmetric centers at any of the carbon atoms including any one of the R substituents and/or exhibit polymorphism. Consequently, compounds of formula I can exist in enantiomeric, or diastereomeric forms, or in mixtures thereof. The processes for preparation can utilize racemates, enantiomers, or diastereomers as starting materials. When diastereomeric or enantiomeric products are prepared, they can be separated by conventional methods for example, chromatographic or fractional crystallization.

"Stable compound" and "stable structure" are meant to indicate a compound that is sufficiently robust to survive isolation, use and storage to a useful degree of purity from a reaction mixture, and formulation into an efficacious therapeutic agent. The present invention is intended to embody stable compounds.

"Therapeutically effective amount" is intended to include an amount of a compound of the present invention alone or an amount of the combination of compounds claimed or an amount of a compound of the present invention in combination with other active ingredients effective to inhibit MCP-1 or effective to treat or prevent inflammatory disorders.

As used herein, "treating" or "treatment" cover the treatment of a disease-state in a mammal, particularly in a human, and include: (a) preventing the disease-state from occurring in a mammal, in particular, when such mammal is predisposed to the disease-state but has not yet been diagnosed as having it; (b) inhibiting the disease-state, i.e., arresting it development; and/or (c) relieving the disease-state, i.e., causing regression of the disease state.

SYNTHESIS

The compounds of the present invention can be prepared in a number of ways well known to one skilled in the art of organic synthesis. The compounds of the present invention can be synthesized using the methods described below, together with synthetic methods known in the art of synthetic organic chemistry, or variations thereon as appreciated by those skilled in the art. Preferred methods include, but are not limited to, those described below. All references cited herein are hereby incorporated in their entirety herein by reference.

The novel compounds of this invention may be prepared using the reactions and techniques described in this section. The reactions are performed in solvents appropriate to the reagents and materials employed and are suitable for the transformations being effected. Also, in the description of the synthetic methods described below, it is to be understood that all proposed reaction conditions, including choice of solvent, reaction atmosphere, reaction temperature, duration of the experiment and work up procedures, are chosen to be the conditions standard for that reaction, which should be readily recognized by one skilled in the art. It is understood by one skilled in the art of organic synthesis that the functionality present on various portions of the molecule must be compatible with the reagents and reactions proposed. Such restrictions to the substituents that are compatible with the reaction conditions will be readily apparent to one skilled in the art and alternate methods must then be used. This will sometimes require a judgment to modify the order of the synthetic steps or to select one particular process scheme over another in order to obtain a desired compound of the invention. It will also be recognized that another major consideration in the planning of any synthetic route in this field is the judicious choice of the protecting group used for protection of the reactive functional groups present in the compounds described in this invention. An authoritative account describing the many alternatives to the trained practitioner is Greene et al. (*Protective Groups In Organic Synthesis*, Third Edition (Wiley and Sons, 1999)).

Some compounds of Formula (I) can be prepared by the routes outlined in Scheme 1. Allylation of the ester starting material 2.1 can be achieved by treating with a base such as lithium diisopropylamide (LDA) followed by allyl bromide to give compound 2.2. Deprotonation of 2.2 with LDA again and reaction of propargyl bromide should provide ester intermediate 2.3. The propargylation of the hindered enolate generated from 2.2 can be accelerated with the presence of hexamethylphosphoramide. The olefin moiety in 2.3 can be selectively degraded via ozonolysis and reductive workup such as triphenylphosphine. The resulting aldehyde 2.4 can be coupled with functionalized benzylamine under reductive conditions using sodium triacetoxyborohydride or sodium cyanoborohydride to give intermediate 2.5. Subsequent treatment with a base such as sodium methoxide should yield the γ-lactam intermediate 2.6. Following partial reduction of the acetylene with Lindlar's catalyst, the resulting olefin 2.7 can be degraded under ozonolysis conditions to yield the penultimate intermediate 2.8. Finally, reductive amination with amines (HNR²R³) using sodium triacetoxyborohydride or sodium cyanoborohydride should complete the synthesis of compounds 2.9.

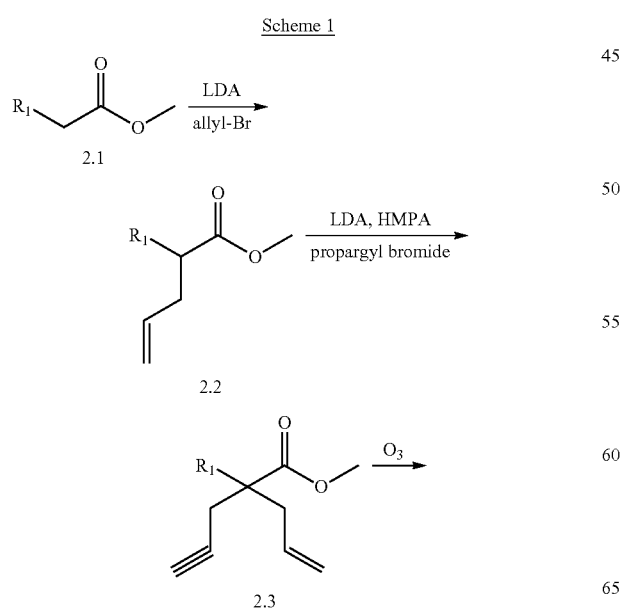

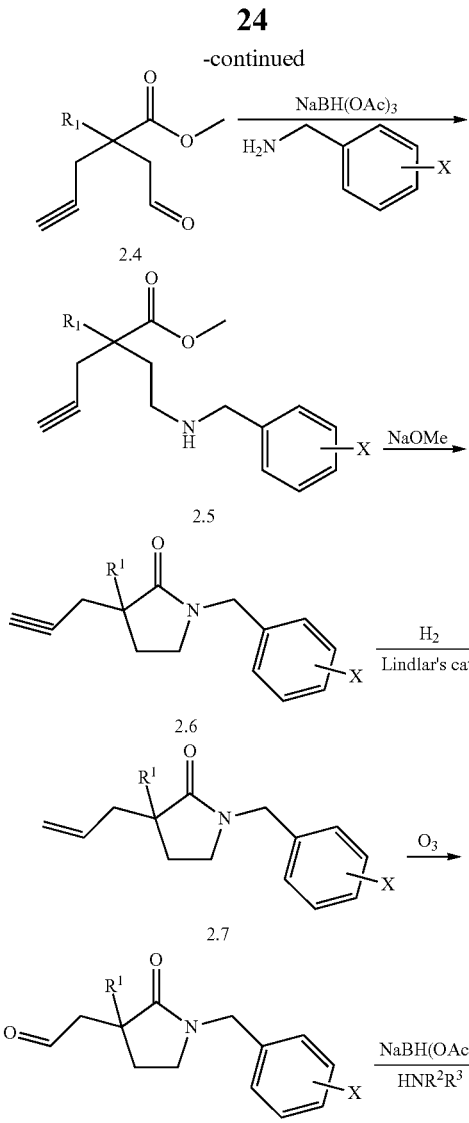

Some compounds of Formula (I) can be prepared by the routes outlined in Scheme 2. Treatment of the enolate of ester 2.2 generated from LDA with tert-butyl bromoacetate in the presence of HMPA should provide intermediate 3.1. After hydrolysis of the tert-butyl ester group with trifluoroacetic acid, the resulting acid 3.2 can be coupled with O-protected ortho-hydroxylbenzylamines using classical coupling conditions such as ethyl chloroformate. Treatment of compound 3.3 with sodium methoxide should induce formation of cyclic imide 3.4. Mono-reduction of the irnmide with diisopropylaluminum hydride should occur selectively at the less hindered carbonyl group to give intermediate 3.5. The O-protecting group in 3.5 can be removed at this stage. Subsequent treatment with an acid such as trifluoroacetic acid should induce formation of tricyclic core 3.7. The olefin moiety in 3.7 can be degraded under ozonolysis conditions to yield the penultimate intermediate 3.8. Finally, reductive amination with amines (HNR²R³) using sodium triacetoxyborohydride or sodium cyanoborohydride should complete the synthesis of compounds 3.9.

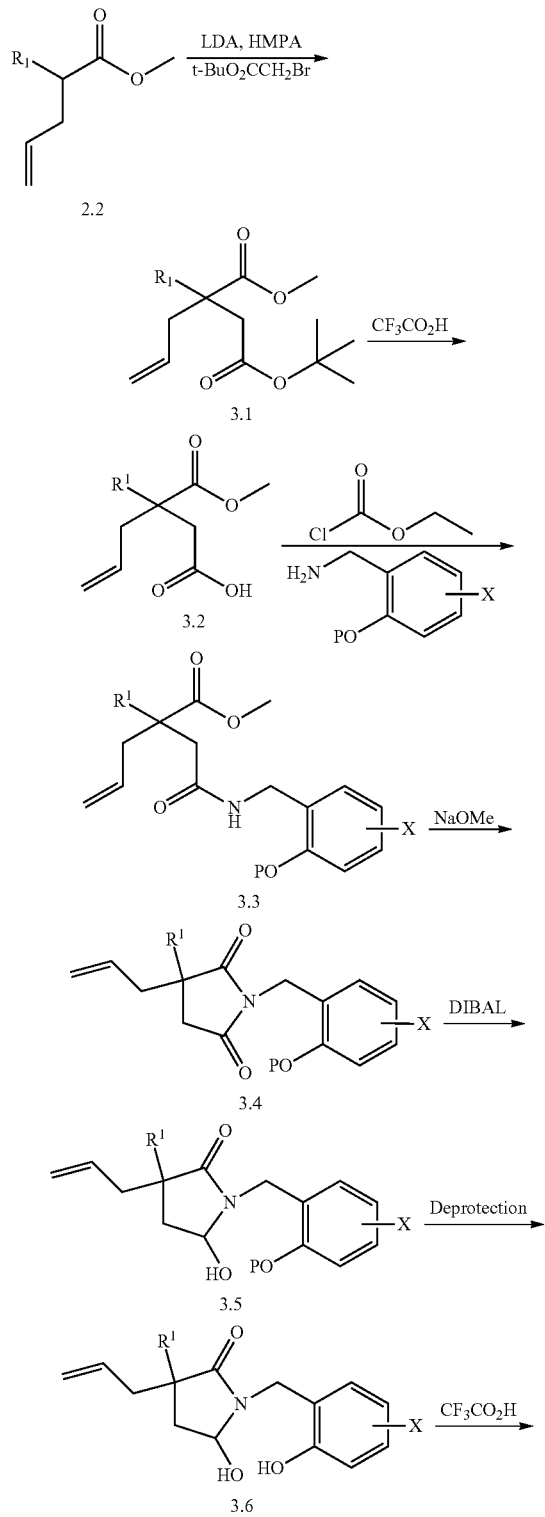

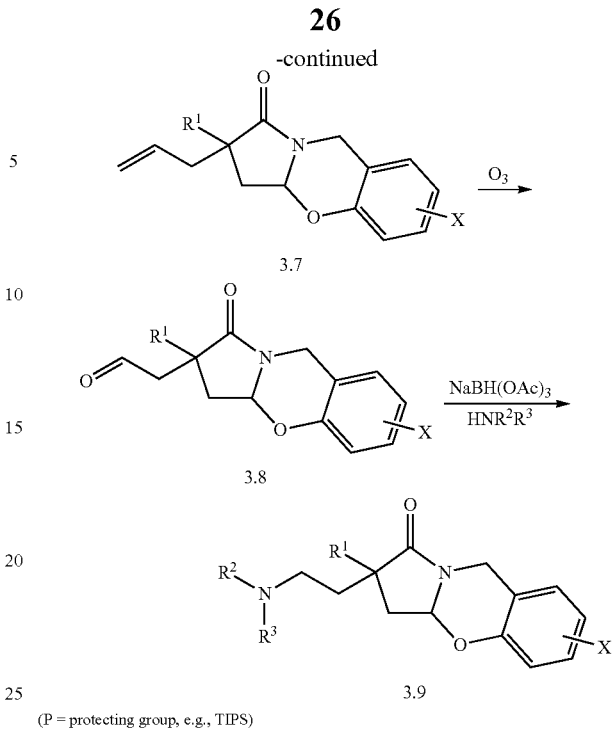

(P = protecting group, e.g., TIPS)

The compounds of Formula (I) contain at least one chiral center, and thus may exist as racemic mixtures or non-racemic mixtures of enantiomers. The two enantiomers may be separated using methods well known in the chemical literature, for example by selective crystallization of a carboxylate salt formed with an optically-active base followed by acidification, or by chromatography on a chiral stationary phase.

Other features of the invention will become apparent in the course of the following descriptions of exemplary embodiments that are given for illustration of the invention and are not intended to be limiting thereof.

EXAMPLES

Abbreviations used in the Examples are defined as "2 x" for twice, "° C." for degrees Celsius, "g" for gram or grams, "mmol" for millimolar, "mL" for milliliter or milliliters, "M" for molar, "min" for minute or minutes, "mg" for milligram or milligrams, "h" for hour or hours, "LC" for liquid chromatography, "HPLC" for high performance liquid chromatography, "MS" for mass spectroscopy, "RT" for room temperature, "THF" for tetrahydrofuran, "Et₂O" for diethyl ether, "NH₄Cl" for ammonium chloride, "EtOAc" for ethyl acetate, "Na₂SO₄" for sodium sulfate, "DMSO" for dimethylsulfoxide, "K₂CO₃" for potassium carbonate, "CH₂Cl₂" for methylene chloride, "TFA" for trifluoroacetic acid, "sat." for saturated, "NaHCO₃" for sodium bicarbonate, "N" for normal, "NaOH" for sodium hydroxide, "MeOH" for methanol, "NaCNBH3" for sodium cyanoborohydride, "MgSO₄" for magnesium sulfate, "NaBH₄" for sodium borohydride, "Hex" for hexane, "H₂O" for water, "HCl" for hydrochloric acid, "AcOH" for acetic acid, "v/v" for volume to volume ratio. "D", "L", "R" and "S" are stereochemical designations familiar to those skilled in the art. Chemical names were derived using ChemDraw Ultra, version 9.0.5. When this program failed to provide a name for the exact structure in question, an appropriate name was assigned using the same methodology utilized by the program.

Intermediate A Synthesis of 3-allyl-1-(3,5-bis(trifluoromethyl)benzyl)-3-isopropylpyrrolidin-2-one

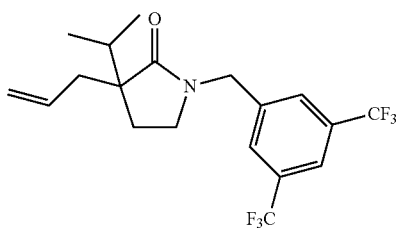 [SMILES: C=CCC1(C(C)C)CCN(Cc2cc(C(F)(F)F)cc(C(F)(F)F)c2)C1=O]

Intermediate A, Step 1: To a stirred solution of diisopropylamine (26.4 ml, 0.19 mol) in THF (150 ml) was added n-butyllithium (60.4 ml, 2.85 M solution in hexane, 0.172 mol) dropwise at −15° C. and the reaction mixture was stirred at −15° C. for 1 h. The reaction mixture was cooled to −78° C. and added a solution of methyl isovalerate (20 g, 0.172 mol) in THF (50 ml) dropwise and stirred at same temperature for 1 h. Added Allyl bromide (16.3 ml, 0.19 mol) followed by HMPA (9.2 g, 0.0516 mol) and stirred at −78° C. for 1 h and allowed to warm to −70° C. over a period of 2 h. The reaction mixture was quenched with 1.5 N HCl and extracted with ethyl acetate (2×500 ml). The combined organic extracts were washed with water, brine, dried over sodium sulphate and concentrated to give the product as a pale brown liquid (19 g, 71%). $^1$H NMR (CDCl$_3$, 400 MHz) δ 5.71-5.78 (m, 1H), 4.98-5.08 (m, 2H), 3.68 (s, 3H), 2.21-2.34 (m, 3H), 1.86-1.91 (m, 1H), 0.92-0.97 (dd, 6H). GC-MS: 156.

Intermediate A, Step 2: To a solution of diisopropylamine (4.28 ml, 0.030 mol) in THF (20 ml) was added n-butyl lithium (10.4 ml, 2.7 M solution in hexane, 0.028 mol) drop wise at −20° C. The reaction mixture was stirred at −20° C. for 1 h. Cooled to −78° C. and added a solution of step-1 compound (4.0 g, 0.025 mol) in THF (20 ml) drop wise. The reaction mixture was stirred at −78° C. for 2 h. Propargyl bromide (3.8 g, 0.032 mol) was added drop wise followed by HMPA (1.37 g, 0.0077 mol) and stirred at −78° C. for 1 h and allowed to warm to RT over night. The reaction mixture was quenched with 1N HCl and extracted with ethyl acetate (2×200 ml). Combined organic layer was washed with water, brine, dried over sodium sulphate and concentrated. Column chromatography of the crude using 5% ethyl acetate in pet ether gave desired product as a yellow liquid (2.5 g, 55%). $^1$H NMR (CDCl$_3$, 400 MHz) δ 5.69-5.73 (m, 1H), 5.14-5.19 (d, 1H), 5.07-5.10 (d, 1H), 3.69 (s, 3H), 2.63-2.68 (m, 1H), 2.55-2.57 (d, 2H), 2.43-2.48 (m, 1H), 2.02-2.09 (m, 1H), 1.98 (s, 1H), 0.98 (d, 6H). GC-MS: 194.

Intermediate A, Step 3: A solution of step-2 compound (14 g, 0.072 mol) in dry dichloromethane (400 ml) was cooled to −78° C. and purged with ozone gas for 3 h. Triphenyl phosphine (45.3 g, 0.173 mol) was added and the reaction mixture was stirred at RT over night. Reaction mixture was diluted with dichloromethane (250 ml), washed with brine, dried over sodium sulphate and concentrated. To the residue was extracted with pet ether, concentrated and purified by column chromatography using 5% ethyl acetate in pet ether to afford 8.0 g (57%) of the product as a yellow liquid. $^1$H NMR (CDCl$_3$, 400 MHz) δ 9.83 (s, 1H), 3.72 (s, 3H), 2.97-3.02 (d, 1H), 2.79-2.88 (t, 2H), 2.67-2.73 (d, 1H), 2.03-2.10 (m, 1H), 2.02 (s, 1H), 0.95 (d, 6H). GC-MS: 196.

Intermediate A, Step 4: A mixture of step-3 compound (6.2 g, 0.0316 mol) and 3,5-bis(trifluoromethyl)benzylamine (7.7 g, 0.0316 mol) in methanol (150 ml) were stirred at RT for 8 h. Reaction mixture was cooled to 0° C. and added sodium borohydride (1.56 g, 0.041 mol) and stirred at RT over night. Solvent was removed under vacuum, added 10% NaHCO$_3$ and the product was extracted with ethyl acetate (250 ml) and concentrated. The crude product was purified by column chromatography using pet ether/ethyl acetate (8:2) as eluent to get the product as a yellow liquid (11.5 g, 86%). $^1$ NMR (CDCl$_3$, 400 MHz) δ 7.81 (s, 2H), 7.76 (s, 1H), 3.86-3.9 (m, 2H), 3.65 (s, 3H), 2.74-2.80 (m, 1H), 2.52-2.68 (m, 3H), 2.15-2.18 (m, 1H), 2.05-2.08 (m, 1H), 1.93-1.98 (m, 2H), 0.92-0.98 (dd, 6H). LC-MS (M+1)$^+$424.1.

Intermediate A, Step 5: To a solution of step-4 compound (10 g, 0.023 mol) in THF (150 ml) and water (75 ml) was added methanol (150 ml) followed by lithium hydroxide (2.2 g, 0.094 mol) in portions and the reaction mixture was stirred at RT for 4 h. Reaction mixture was concentrated to half the volume, diluted with water and extracted with ethyl acetate (2×250 ml). Combined organic extracts were washed with water, brine, dried over sodium sulphate and concentrated to get the product as a white solid. (7.5 g, 81%). $^1$H NMR (CDCl$_3$, 400 MHz) δ 7.81 (s, 1H), 7.77 (s, 2H), 4.89-4.93 (d, 1H), 4.34-4.38 (d, 1H), 3.27-3.33 (m, 1H), 2.55-2.60 (d, 1H), 2.42-2.47 (d, 1H), 2.03-2.12 (m, 3H), 1.90 (s, 1H), 0.9 (d, 6H). LC-MS (M+1)$^+$ 392.0.

Intermediate A, Step 6: To a solution of step-5 compound (7.5 g, 0.019 mol) in methanol (300 ml) was added Lindlar catalyst (1.0 g) and the reaction mixture was hydrogenated for 2 h. The reaction mixture was filtered over Celite and the filtrate was concentrated. Crude was purified by column chromatography using pet ether/ethyl acetate (9:1) as eluent to get the product as a white solid. (6.0 g, 80%). $^1$H NMR (CDCl$_3$, 400 MHz) δ 7.80 (s, 11t), 7.70 (s, 2H), 5.67-5.77 (m, 1H), 5.04-5.14 (m, 2H), 4.64-4.68 (d, 1H), 4.47-4.51 (d, 1H), 3.09-3.14 (m, 2H), 2.39-2.44 (m, 1H), 2.20-2.26 (m, 1H), 2.02-2.09 (m, 1H), 1.94-2.00 (m, 1H), 1.79-1.83 (m, 1H), 0.90-0.92 (d, 3H), 0.86-0.88 (d, 3H). LC-MS (M+1)$^+$ 394.1.

Example 1a 1-(3,5-bis(trifluoromethyl)benzyl)-3-isopropyl-3-(2-(piperidin-1-yl)ethyl)pyrrolidin-2-one, TFA Salt

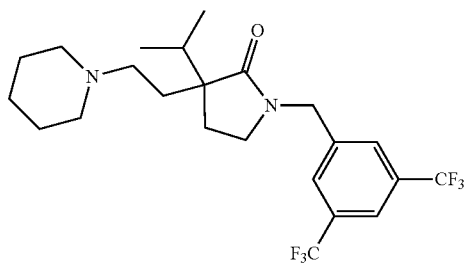 [SMILES: CC(C)C1(CCN2CCCCC2)CCN(Cc2cc(C(F)(F)F)cc(C(F)(F)F)c2)C1=O]

Example 1a, Step 1: A solution of 3-allyl-1-(3,5-bis(trifluoromethyl)-benzyl)-3-isopropylpyrrolidin-2-one (1.0 g, 2.54 mmol) in acetone (9 mL) was cooled to −78° C. O$_3$ was bubbled through this solution until the color had changed from colorless to blue (30 min). At this point nitrogen gas was bubbled through the solution for 5 minutes, and dimethyl sulfide (1.88 mL, 25.4 mmol) was added. The solution was allowed to warm to room temperature over 2 h, and then concentrated in vacuo to yield impure 2-(1-(3,5-bis(trifluoromethyl)benzyl)-3-isopropyl-2-oxopyrrolidin-3-yl)acetaldehyde as a clear oil. Key non-solvent resonances in $^1$H-NMR (400 MHz, CDCl$_3$) δ=9.81 (s, 1H), 8.0-7.8 (m, 3H), 5.2-5.0 (m, 1H), 4.7-4.5 (m, 1H), 3.4-3.1 (m, 2H), 2.2-1.8 (m, 5H), 1.0-0.8 (m, 6H).

Example 1a, Step 2: A solution of the crude 2-(1-(3,5-bis(trifluoromethyl)-benzyl)-3-isopropyl-2-oxopyrrolidin-3-yl)acetaldehyde (one sixth the material from step 1, approximately 0.39 mmol) in CH$_2$Cl$_2$ (2.3 mL) was charged with piperidine (40 mg, 0.47 mmol), NaHB(OAc)$_3$ (166 mg, 0.78 mmol) and 4 angstrom molecular sieves (300 mg). The reaction was stirred for 3 h and then diluted with CH$_2$Cl$_2$ (5 mL) and washed 2× with sat. NaHCO$_3$ (10 mL). The organic layer was dried (Na$_2$SO$_4$), filtered, and concentrated in vacuo. The residue was purified by reverse phase HPLC to afford the title compound (86 mg, 38%). LC/MS [M+H]$^+$=465.22. HPLC t$_R$=1.66 min [Waters Sunfire C18 4.6×50 mm column, 3 min gradient from 10/90/0.1 MeOH/H$_2$O/TFA to 90/10/0.1 MeOH/H$_2$O/TFA at 4 mL/min flow rate]. $^1$H-NMR (400 MHz, MeOD) δ=7.97 (s, 11H), 7.94 (s, 2H), 4.82 (d, J=15.0 Hz, 1H), 4.50 (d, J=15.0 Hz, 1H), 3.7-3.0 (m, 8H), 2.2-1.6 (m, 11H), 0.96 (d, J=6.8 Hz, 3H), 0.86 (d, J=6.8 Hz, 3H).

Examples 1b-1c

Examples 1b-1c were made using the methods exemplified above in Example 1a. Data for Examples 1b-1c are provided in Table 1 below. The substituents listed in each column are to be paired with the structure embedded in the table heading. In the synthesis of the examples, substitutions for key reagents were made in Step 2 of the procedure outlined in Example 1a, as will be evident to one skilled in the art. The data in the "MS" column represent the values observed for the (M+H)$^+$ ions in electrospray mass spectroscopy experiments. For mass spectra in which multiple isotopes were observed, the major ion is listed. The data in the "HPLC" column indicate the retention time under the following HPLC conditions: Waters Sunfire C18 4.6×50 mm column, 3 min gradient from 10/90/0.1 MeOH/H$_2$O/TFA to 90/10/0.1 MeOH/H$_2$O/TFA at 4 mL/min flow rate.

TABLE 1

| Example | R | MS | HPLC |
|---|---|---|---|
| Example 1b: 1-(3,5-bis(trifluoromethyl)benzyl)-3-isopropyl-3-(2-(4-phenylpiperidin-1-yl)ethyl)pyrrolidin-2-one, TFA salt | | 541.34 | 1.78' |

TABLE 1-continued

| Example | R | MS | HPLC |
|---|---|---|---|
| Example 1c: 1-(3,5-bis(trifluoromethyl)benzyl)-3-isopropyl-3-(2-((1R,3'R)-3'-methylspiro[indene-1,4'-piperidine]-1'-yl)ethyl)pyrrolidin-2-one, TFA salt | | 579.31 | 1.88' |

Example 2a 1-(3,5-bis(trifluoromethyl)benzyl)-3-isopropyl-3-(3-(4-phenylpiperidin-1-yl)propyl)pyrrolidin-2-one, TFA Salt Example 2a, Step 1: A solution of 3-allyl-1-(3,5-bis(trifluoromethyl)-benzyl)-3-isopropylpyrrolidin-2-one (1.12 g, 2.85 mmol) was dissolved in tetrahydrofuran (14 mL) and cooled to 0° C. The resultant solution was charged with borane tetrahydrofuran complex (1 M in THF, 1.42 mL, 1.42 mmol) dropwise. The resulting solution was allowed to warm to room temperature with stirring for 14 h. At this time the reaction was charged with sodium perborate (0.66 g, 4.27 mmol) and water (1.4 mL). The mixture was stirred for ~2 h, and partitioned between sat. NaCl and EtOAc. The aqueous phase was extracted once more with EtOAc. The organic extracts were combined, dried (MgSO$_4$), filtered, and concentrated in vacuo. The crude 1-(3,5-bis(trifluoromethylbenzyl)-3-(3-hydroxypropyl)-3-isopropylpyrrolidin-2-one was taken on without further purification to step 2. LC/MS [M+H]$^+$=412.22. HPLC t$_R$=1.94 min [Waters Sunfire C18 4.6×50 mm column, 3 min gradient from 10/90/0.1 MeOHiH$_2$O/TFA to 90/10/0.1 MeOH/H$_2$O/TFA at 4 mL/min flow rate].

Example 2a, Step 2: To a solution of 1-(3,5-bis(trifluoromethyl)benzyl)-3-(3-hydroxypropyl)-3-isopropylpyrrolidin-2-one (1.1 g, approximately 2.67 mmol) in CH$_2$Cl$_2$ (27 mL)

was added tetra-n-propylammonium perruthenate (47 mg, 0.134 mmol), N-methylmorpholine N-oxide (0.626 g, 5.35 mmol) and 4 angstrom molecular sieves (0.31 g). After 30 minutes stirring, the solution was filtered through celite and concentrated to provide 3-(1-(3,5-bis(trifluoromethyl)benzyl)-3-isopropyl-2-oxopyrrolidin-3-yl)propanal as an impure dark oil that was used in step 3 without further purification. LC/MS [M+H]$^+$=410.15. HPLC $t_R$=1.96 min [Waters Sunfire C18 4.6×50 mm column, 3 min gradient from 10/90/0.1 MeOH/H$_2$O/TFA to 90/10/0.1 MeOH/H$_2$O/TFA at 4 mL/min flow rate].

Example 2a, Step 3: To a solution of 3-(1-(3,5-bis(trifluoromethyl)benzyl)-3-isopropyl-2-oxopyrrolidin-3-yl)propanal (110 mg, 0.27 mmol) in CH$_2$Cl$_2$ (1.7 mL) was added 4-phenylpiperidine (52 mg, 0.32 mmol), NaHB(OAc)$_3$ (114 mg, 0.54 mmol) and 4 angstrom molecular sieves (200 mg). The reaction was stirred for 3 h and then diluted with CH$_2$Cl$_2$ (5 mL) and washed 2× with sat. NaHCO$_3$ (10 mL). The organic layer was dried (Na$_2$SO$_4$), filtered, and concentrated in vacuo. The residue was purified by reverse phase HPLC to afford the title compound (12.7 mg, 7.1%). LC/MS [M+H]= 555.33. HPLC $t_R$=1.84 min [Waters Sunfire C18 4.6×50 mm column, 3 min gradient from 10/90/0.1 MeOH/H$_2$O/TFA to 90/10/0.1 MeOH/H$_2$O/TFA at 4 mL/min flow rate]. $^1$H-NMR (400 MHz, MeOD) δ=7.84 (s, 1H), 7.81 (s, 2H), 7.24-7.10 (m, 5H), 4.70 (d, J=15.0 Hz, 1H), 4.38 (d, J=15.0 Hz, 1H), 3.55 (t, J=12.0 Hz, 2H), 3.3-2.8 (m, 7H), 2.1-1.7 (m, 11H), 0.83 (d, J=6.8 Hz, 3H), 0.75 (d, J=6.8 Hz, 3H).

Intermediate B (5-(trifluoromethyl)-2-(triisopropylsilyloxy)phenyl)methanamine, HCl Salt

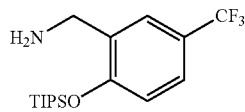

Intermediate B, Step 1: A 250-mL round bottom flask containing a magnetic stir bar and fitted with a condenser and a inert gas inlet was charged successively with sodium hydride (60% dispersion in mineral oil, 1.32 g, 33.0 mmol), THF (46 mL) and a THF (46 mL) solution of benzyl alcohol (2.86 mL, 27.5 mmol) and 2-fluoro-5-(trifluoromethyl)benzonitrile (5.2 g, 27.5 mmol). The resulting solution was warmed to 60° C. for 3 h, then cooled to RT, diluted with EtOAc (200 mL) and washed with water (2×100 mL) and brine (60 mL). The organic layer was dried (MgSO$_4$) and concentrated on a rotary evaporator to give crude 2-(benzyloxy)-5-(trifluoromethyl)benzonitrile (7.32 g, 26.4 mmol, 96% yield) as a colorless oil. LC/MS [M+H]$^+$=278.07. $^1$H-NMR (400 MHz, CDCl$_3$) δ=7.89 (s, 1H), 7.78 (d, J=12.0 Hz, 1H), 7.5-7.3 (m, 5H), 7.12 (d, J=8.0 Hz, 1H), 5.31 (s, 2H).

Intermediate B, Step 2: A 250-mL round bottom flask containing a magnetic stir bar was charged successively with 2-(benzyloxy)-5-(trifluoromethyl)benzonitrile (7.30 g, 26.3 mmol), ethanol (76 mL) and 10 wt % palladium on carbon (560 mg, 5.27 mmol). The resulting solution was put under a hydrogen atmosphere and stirred for 3 h. The solution was then filtered and evaporated until all ethanol was removed. The residue was redissolved in DMF (38 mL), and chlorotriisopropylsilane (9.02 mL, 42.1 mmol) and imidazole (2.87 g, 42.1 mmol) were added and stirred for 4 h. At this time the solution was diluted with diethyl ether (300 mL) and washed with brine (5×100 mL). The organic layer was dried (MgSO$_4$) and concentrated on a rotary evaporator. The residue was purified using a 120 g silica gel cartridge and 20:1 Hex/EtOAc to 4:1 Hex/EtOAc to elute 5-(trifluoromethyl)-2-(triisopropylsilyloxy)benzonitrile (8.80 g, 25.6 mmol, 97% yield) as a colorless oil. LC/MS [M+H]-=344.19. $^1$H-NMR (400 MHz, CDCl$_3$) δ=7.83 (s, 1H), 7.70 (dd, J=8.0, 3.6 Hz, 1H), 7.03 (d, J=8.0 Hz, 1H), 1.15-1.0 (m, 21H).

Intermediate B, Step 3: A 250-mL round bottom flask was charged successively with 5-(trifluoromethyl)-2-(triisopropylsilyloxy)benzonitrile (7.30 g, 26.3 mmol), ethanol (66 mL), CHCl$_3$ (3.3 mL) and platinum oxide (635 mg, 2.80 mmol). The resulting suspension was put under a hydrogen atmosphere and stirred for 36 h. The solution was then filtered and evaporated until all ethanol was removed. The residue was redissolved in DMF (38 mL), and concentrated on a rotary evaporator, providing (5-(trifluoromethyl)-2-(triisopropylsilyloxy)phenyl)methanamine, HCl salt (4.61 g, 13.3 mmol, 95% yield) as a white solid. LC/MS [M+H]$^+$=348.13, HPLC $t_R$=1.84 min [Waters Sunfire C18 4.6×50 mm column, 3 min gradient from 10/90/0.1 MeOH/H$_2$O/TFA to 90/10/0.1 MeOH/H$_2$O/TFA at 4 mL/min flow rate].

Intermediate C 3-isopropyl-3-(methoxycarbonyl)hex-5-enoic Acid

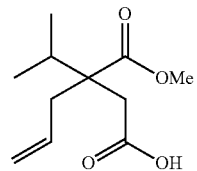

Intermediate C, Step 1: To a stirred solution of LDA [which was prepared by addition of n-butyllithium (104 ml, 0.30 mol; 2.9 M solution in hexane) to a solution of diisopropylamine (46.6 ml, 0.33 mol) in THF (400 ml) at −20° C.] was added a solution of methyl 2-isopropylpent-4-enoate (43 g, 0.27 mol) in THF (200 ml) at −78° C. The reaction mixture was warmed up to −50° C. in 1 h and cooled to −78° C. tert-Butyl bromoacetate (64.4 g, 0.33 mol) was added dropwise followed by HMPA (14.8 g, 0.083 mol). The reaction mixture was stirred at −78° C. for 1 h, allowed to warm up to 0° C., quenched with saturated NH$_4$Cl solution and extracted with ethyl acetate. The organic extracts were washed with water, brine, dried over sodium sulphate and concentrated. Purified by column chromatography using petroleum ether/ethyl acetate (95:5) as eluent to get 50 g (67%) of the product as yellow oil. $^1$H NMR (400 MHz, CDCl$_3$) δ 5.78-5.85(m, 1H), 5.05-5.10 (m, 2H), 3.69 (s, 3H), 2.77-2.81(d, 1H), 2.56-2.58(m, 2H), 2.35-2.39 (d, 1H), 1.91-1.95(m, 1H), 1.42 (s, 9H), 0.90-0.92 (d, 6H). $^{13}$C NMR (100 MHz, CDCl$_3$) δ 17.9, 28.0, 33.3, 36.3, 39.3, 50.6, 51.3, 80.4, 118.2, 134.5, 170.8, 175.1 GCMS 271 (M+1)$^+$ Intermediate C, Step 2: The product from Step 1 (50 g, 0.185 mol) in dichloromethane (500 ml) was treated with trifluoroacetic acid (300 ml). The reaction mixture was stirred at RT for 20 h. Solvent was removed under reduced pressure and the crude product was purified by column chromatography using 25% of EtOAc in hexane as eluent to get 37 g (94%) of the product as yellow liquid. $^1$H NMR (400 MHz, CDCl$_3$) δ 9.0-10.2 (b, 1H), 5.75-5.82 (m, 1H), 5.06-5.11 (m, 2H), 3.70

(s, 3H), 2.85-2.89 (d, 1H), 2.49-2.60 (m, 3H), 1.96-1.99 (m, 1H), 0.91-0.94 (d, 6H). $^{13}$C NMR (100 MHz, CDCl$_3$) δ 17.8, 33.4, 36.6, 37.5, 50.7, 51.7, 118.7, 133.9, 175.2, 177.4. GCMS 215 (M+1)$^+$.

Example 3a

Synthesis of 2-(2-(tert-butylamino)ethyl)-2-isopropyl-7-(trifluoromethyl)-2,3,3,a,9-tetrahydro-1H-benzo[e]pyrrolo[2,1-b][1,3]oxazin-1-one, TFA Salt

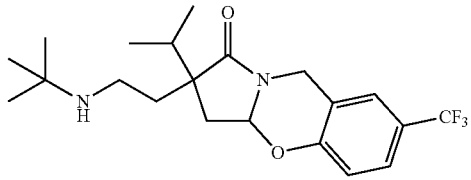 [SMILES: CC(C)C1(CCNC(C)(C)C)CC2Oc3ccc(C(F)(F)F)cc3CN2C1=O]

Example 3a, Step 1: A solution of 3-isopropyl-3-(methoxycarbonyl)hex-5-enoic acid (1.95 g, 9.10 mmol) in THF (46 mL) was cooled to 0° C. under nitrogen atmosphere. The solution was treated dropwise with ethyl chloroformate (0.874 mL, 9.10 mmol) and triethylamine (2.54 mL, 18.2 mmol) successively via syringe over 3 min. The resulting mixture was stirred at RT for 1 h. At this time the reaction was charged with (5-(trifluoromethyl)-2-(triisopropylsilyloxy) phenyl)methanamine, HCl salt (3.16 g, 9.10 mmol) and stirred for 3 h. At this time the mixture was diluted with EtOAc (100 mL) and sat. NaHCO$_3$ (50 mL) and the phases separated. The organic phase was washed with brine, dried (MgSO$_4$) and concentrated on a rotary evaporator. The residue was purified using a 80 g silica gel cartridge and 20:1 Hex/EtOAc to 1:1 Hex/EtOAc to elute methyl 2-isopropyl-2-(2-oxo-2-(5-(trifluoromethyl)-2-(triisopropylsilyloxy) benzylamino)ethyl)pent-4-enoate (2.41 g, 4.43 mmol, 49% yield) as a white solid. LC/MS [M+H]$^+$=544.22, HPLC t$_R$=1.87 min [Waters Sunfire C18 4.6×50 mm column, 3 min gradient from 10/90/0.1 MeOH/H$_2$O/TFA to 90/10/0.1 MeOH/H$_2$O/TFA at 4 mL/min flow rate].

Example 3a, Step 2: A 100 mL round bottom flask charged with 2-isopropyl-2-(2-oxo-2-(5-(trifluoromethyl)-2-(triisopropylsilyloxy)benzylamino)-ethyl)pent-4-enoate (1.40 g, 2.57 mmol) in MeOH (26 mL) was cooled to 0° C. The solution was treated dropwise with sodium methoxide (25% solution in MeOH, 0.048 mL, 0.206 mmol) via syringe over 3 min, and the resulting mixture was stirred for 12 h. At this time mixture was diluted with EtOAc (100 mL) washed with brine (2×20 mL). The organic layer was dried (MgSO$_4$) and concentrated on a rotary evaporator. The residue was purified using a 12 g silica gel cartridge and 20:1 Hex/EtOAc to 3:1 Hex/EtOAc to elute 3-allyl-3-isopropyl-1-(5-(trifluoromethyl)-2-(triisopropylsilyloxy)benzyl)pyrrolidine-2,5-dione (538 mg, 1.05 mmol, 41% yield) as a clear oil. LC/MS [M+H]$^+$=512.12, HPLC t$_R$=2.55 min [Waters Sunfire C18 4.6×50 mm column, 3 min gradient from 10/90/0.1 MeOH/H$_2$O/TFA to 90/10/0.1 MeOH/H$_2$O/TFA at 4 mL/min flow rate]. $^1$H-NMR (400 MHz, CDCl$_3$) δ=7.38 (d, J=8.0 Hz, 1H), 7.14 (s, 1H), 6.88 (d, J=8.0 Hz, 1H), 5.67 (m, 1H), 5.19 (m, 2H), 4.75 (s, 2H), 2.56 (m, 2H), 2.35 (m, 1H), 2.17 (m, 2H), 1.16 (m, 2H), 0.98 (d, J=6.8 Hz, 3H), 0.92 (d, J=6.8 Hz, 3H).

Example 3a, Step 3: A solution of 3-allyl-3-isopropyl-1-(5-(trifluoromethyl)-2-(triisopropylsilyloxy)benzyl)pyrrolidine-2,5-dione (538 mg, 1.05 mmol) in toluene (18 mL) under argon was cooled to −78° C. The solution was treated dropwise with diisobutylaluminum hydride (1M solution in toluene, 18 mL, 2.63 mmol) via syringe over 5 min, and the resulting mixture was stirred for 2 h. At this time the mixture was quenched with 0.5 mL MeOH, warmed to room temperature, concentrated on a rotary evaporator, and the resulting 3-allyl-5-hydroxy-3-isopropyl-1-(5-(trifluoromethyl)-2-(triisopropylsilyloxy)benzyl)pyrrolidin-2-one brought forward to step 4 as an impure oil. LC/MS [M+H]$^+$=514.29, HPLC t$_R$=2.31 min [Waters Sunfire C18 4.6×50 mm column, 3 min gradient from 10/90/0.1 MeOH/H$_2$O/TFA to 90/10/0.1 MeOH/H$_2$O/TFA at 4 mL/min flow rate].

Example 3a, Step 4: A solution of 3-allyl-5-hydroxy-3-isopropyl-1-(5-(trifluoromethyl)-2-(triisopropylsilyloxy) benzyl)pyrrolidin-2-one (approximately 525 mg, 1.02 mmol) in THF (13 mL) was charged with tris(dimethylamino)sulfonium difluorotrimethylsilicate (366 mg, 1.33 mmol) and the resulting mixture was stirred for 30 min. At this time the mixture was charged with TFA (0.394 mL, 5.11 mmol) and 4 angstrom molecular sieves (500 mg). This solution was stirred for 12 h, at which time it was diluted with EtOAc and washed 2× with brine. The organic layer was dried (MgSO$_4$) and concentrated on a rotary evaporator. The residue was purified using a 12 g silica gel cartridge and 20:1 Hex/EtOAc to 3:1 Hex/EtOAc to elute 2-allyl-2-isopropyl-7-(trifluoromethyl)-2,3,3a,9-tetrahydro-1H-benzo[e]pyrrolo[2,1-b][1,3] oxazin-1-one (177 mg, 0.52 mmol, 51% yield) as a clear oil, 1:1 mixture of diastereomers. LC/MS [M+H]$^+$=340.15, HPLC t$_R$=1.99 min [Waters Sunfire C18 4.6×50 mm column, 3 min gradient from 10/90/0.1 MeOH/H$_2$O/TFA to 90/10/0.1 MeOH/H$_2$O/TFA at 4 mL/min flow rate]. $^1$H-NMR (400 MHz, CDCl$_3$) δ=7.26 (d, J=8.0 Hz, 1H), 7.21 (s, 1H), 6.80 (d, J=8.0 Hz, 1H), 5.56 (m, 1H), 5.2-4.8 (m, 3H), 4.16 (m, 1H), 2.3-1.8 (m, 5H), 0.8-0.6 (m, 6H).

Example 3a, Step 5: A solution of 2-allyl-2-isopropyl-7-(trifluoromethyl)-2,3,3a,9-tetrahydro-1H-benzo[e]pyrrolo [2,1-b][1,3]oxazin-1-one (177 mg, 0.52 mmol) in CH$_2$Cl$_2$ (7 mL) was cooled to −78° C. O$_3$ was bubbled through this solution until the color had changed from colorless to blue (30 min). At this point nitrogen gas was bubbled through the solution for 5 minutes, and dimethyl sulfide (0.39 mL, 5.2 mmol) was added. The solution was allowed to warm to room temperature over 2 h, and then concentrated in vacuo to yield impure 2-(2-isopropyl-1-oxo-7-(trifluoromethyl)-2,3,3a,9-tetrahydro-1H-benzo[e]pyrrolo[2,1-b][1,3]oxazin-2-yl)acetaldehyde as a clear oil. LC/MS [M+H]$^+$=342.19, HPLC t$_R$=1.85 min [Waters Sunfire C18 4.6×50 mm column, 3 min gradient from 10/90/0.1 MeOH/H$_2$O/TFA to 90/10/0.1 MeOH/H$_2$O/TFA at 4 mL/min flow rate].

Example 3a, Step 6: A solution of the crude 2-(2-isopropyl-1-oxo-7-(trifluoromethyl)-2,3,3a,9-tetrahydro-1H-benzo[e] pyrrolo[2,1-b][1,3]oxazin-2-yl)acetaldehyde (one fifth the material from step 1, approximately 0.10 mmol) in CH$_2$Cl$_2$ (3.2 mE) was charged with t-butyl amine (14.2 mg, 0.19 mmol), NaHB(OAc)$_3$ (41 mg, 0.19 mmol) and 4 angstrom molecular sieves (100 mg). The reaction was stirred for 3 h and then diluted with EtOAc (10 mL) and washed 2× with sat. NaHCO$_3$ (5 mL). The organic layer was dried (Na$_2$ SO$_4$), filtered, and concentrated in vacuo. The residue was purified by reverse phase HPLC to afford the title compound (15 mg, 30%). LC/MS [M+H]$^+$=399.33. HPLC t$_R$=1.62/1.80 min (1:1 diastereomers) [Waters Sunfire C18 4.6×50 mm column, 3 min gradient from 10/90/0.1 MeOHlJH$_2$O/TFA to 90/10/0.1 MeOH/H$_2$O/TFA at 4 mL/min flow rate]. $^1$H-NMR (400 MHz, MeOD) δ=7.48 (m, 1H), 7.42 (m, 1H), 6.97 (m, 1H), 5.51 (m, 11-), 4.90 (m, 1H), 4.39 (m, 1H), 3.13 (m, 1H), 28-25 (m, 2H), 2.23 (s, 1H), 2.0-1.8 (m, 4H), 1.30 (s, 9H), 0.90-0.75 (m, 6H).

Examples 3b-3p

Examples 3b-3p were made using the methods exemplified above in Example 3a. Data for Examples 3b-3p are provided in Table 2 below. The substituents listed in each column are to be paired with the structure embedded in the table heading. In the synthesis of the examples, substitutions for key reagents were made in Step 6 of the procedure outlined in Example 3a, as will be evident to one skilled in the art. The data in the "MS" column represent the values observed for the $(M+H)^+$ ions in electrospray mass spectroscopy experiments. For mass spectra in which multiple isotopes were observed, the major ion is listed. The data in the "HPLC" column indicate the retention time (with multiple retention times given for individual diastereomers where possible) under one of the following two sets of HPLC conditions: (A)-Waters Sunfire C18 4.6×50 mm column, 3 min gradient from 10/90/0.1 MeOH/H$_2$O/TFA to 90/10/0.1 MeOH/H$_2$O/TFA at 4 mL/min flow rate; (B)-Phenomenex Gemini 4.6×100 mm 5 um C18, 7 min gradient from 30/70 Acetonitrile/10 mM aq. NH$_4$OAc to 95/5 Acetonitrile/10 mM aq. NH$_4$OAc at 1.2 mL/min flow rate.

TABLE 2

| Example | R | MS | HPLC (Conditions) |
|---|---|---|---|
| Example 3b: 2-isopropyl-2-(2-(4-phenylpiperidin-1-yl)ethyl)-7-(trifluoromethyl)-2,3,3a,9-tetrahydro-1H-benzo[e]pyrrolo[2,1-b][1,3]oxazin-1-one, TFA salt | | 487.21 | 1.59/1.71' (A) |
| Example 3c: 3-(1-(2-(2-isopropyl-1-oxo-7-(trifluoromethyl)-2,3,3a,9-tetrahydro-1H-benzo[e]pyrrolo[2,1-b][1,3]oxazin-2-yl)ethyl)piperidin-4-yl)benzoic acid, TFA salt | | 531.29 | 1.49/1.64' (A) |
| Example 3d: 2-isopropyl-2-(2-(piperidin-1-yl)ethyl)-7-(trifluoromethyl)-2,3,3a,9-tetrahydro-1H-benzo[e]pyrrolo[2,1-b][1,3]oxazin-1-one, TFA salt | | 411.22 | 1.38/1.58' (A) |
| Example 3f: 2-isopropyl-2-(2-(spiro[indene-1,4'-piperidine]-1'-yl)ethyl)-7-(trifluoromethyl)-2,3,3a,9-tetrahydro-1H-benzo[e]pyrrolo[2,1-b][1,3]oxazin-1-one, TFA salt | | 511.32 | 1.65/1.74' (A) |
| Example 3g: 2-isopropyl-2-(2-((1R,3'R)-3'-methylspiro[indene-1,4'-piperidine]-1'-yl)ethyl)-7-(trifluoromethyl)-2,3,3a,9-tetrahydro-1H-benzo[e]pyrrolo[2,1-b][1,3]oxazin-1-one, TFA salt | | 525.34 | 1.66/1.74' (A) |
| Example 3h: 2-isopropyl-2-(2-(tetrahydro-2H-pyran-4-ylamino)ethyl)-7-(trifluoromethyl)-2,3,3a,9-tetrahydro-1H-benzo[e]pyrrolo[2,1-b][1,3]oxazin-1-one, TFA salt | | 427.22 | 1.36/1.58' (A) |

TABLE 2-continued

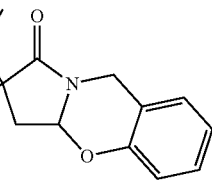

| Example | R | MS | HPLC (Conditions) |
|---|---|---|---|
| Example 3i: 2-(2-((1r,4r)-4-hydroxycyclohexylamino)ethyl)-2-isopropyl-7-(trifluoromethyl)-2,3,3a,9-tetrahydro-1H-benzo[e]pyrrolo[2,1-b][1,3]oxazin-1-one, TFA salt | 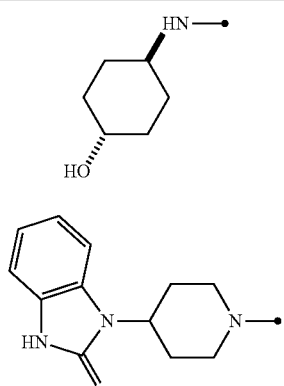 | 441.29 | 1.54/1.78' (A) |
| Example 3j: 2-isopropyl-2-(2-(4-(2-oxo-2,3-dihydro-1H-benzo[d]imidazol-1-yl)piperidin-1-yl)ethyl)-7-(trifluoromethyl)-2,3,3a,9-tetrahydro-1H-benzo[e]pyrrolo[2,1-b][1,3]oxazin-1-one, TFA salt | 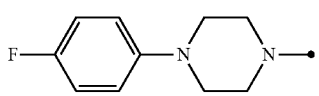 | 543.41 | 4.89' (B) |
| Example 3k: 2-(2-(4-(4-fluorophenyl)piperazin-1-yl)ethyl)-2-isopropyl-7-(trifluoromethyl)-2,3,3a,9-tetrahydro-1H-benzo[e]pyrrolo[2,1-b][1,3]oxazin-1-one, TFA salt | 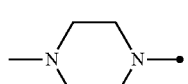 | 506.38 | 6.94' (B) |
| Example 3l: 2-isopropyl-2-(2-(4-methylpiperazin-1-yl)ethyl)-7-(trifluoromethyl)-2,3,3a,9-tetrahydro-1H-benzo[e]pyrrolo[2,1-b][1,3]oxazin-1-one, TFA salt | 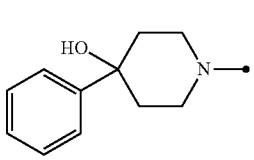 | 426.33 | 3.30' (B) |
| Example 3m: 2-(2-(4-hydroxy-4-phenylpiperidin-1-yl)ethyl)-2-isopropyl-7-(trifluoromethyl)-2,3,3a,9-tetrahydro-1H-benzo[e]pyrrolo[2,1-b][1,3]oxazin-1-one, TFA salt | 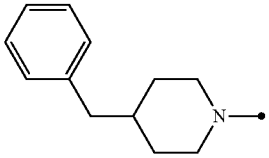 | 503.42 | 4.08' (B) |
| Example 3n: 2-(2-(4-benzylpiperidin-1-yl)ethyl)-2-isopropyl-7-(trifluoromethyl)-2,3,3a,9-tetrahydro-1H-benzo[e]pyrrolo[2,1-b][1,3]oxazin-1-one, TFA salt | 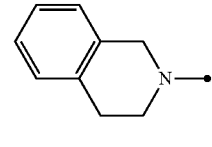 | 501.41 | 5.55' (B) |
| Example 3o: 2-(2-(3,4-dihydroisoquinolin-2(1H)-yl)ethyl)-2-isopropyl-7-(trifluoromethyl)-2,3,3a,9-tetrahydro-1H-benzo[e]pyrrolo[2,1-b][1,3]oxazin-1-one, TFA salt | 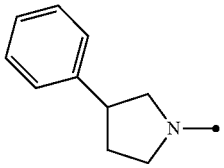 | 459.32 | 6.94' (B) |
| Example 3p: 2-isopropyl-2-(2-(3-phenylpyrrolidin-1-yl)ethyl)-7-(trifluoromethyl)-2,3,3a,9-tetrahydro-1H-benzo[e]pyrrolo[2,1-b][1,3]oxazin-1-one, TFA salt | | 473.24 | 4.87' (B) |

Utility

In general, compounds of the present invention, such as particular compounds disclosed in the preceding examples, have been shown to be modulators of chemokine receptor activity (for example, by displaying Ki values <10,000 nM in a binding assay such as those set forth below). By displaying activity as modulators of chemokine receptor activity, compounds of the present invention are expected to be useful in the treatment of human diseases associated with chemokines and their cognate receptors.

Antagonism of MCP-1 Binding to Human PBMC
(Yoshimura et al., *J. Immunol.* 1990, 145, 292)

Millipore filter plates (#MABVN 1250) are treated with 100 µl of binding buffer (0.5% bovine serum albumin, 20 mM HEPES buffer and 5 mM magnesium chloride in RPMI 1640 media) for thirty minutes at room temperature. To measure binding, 50 µl of binding buffer, with or without a known concentration compound, is combined with 50 µl of $^{125}$-I labeled human MCP-1 (to give a final concentration of 150 pM radioligand) and 50l of binding buffer containing 5×10$^5$ cells. Cells used for such binding assays can include human peripheral blood mononuclear cells isolated by Ficoll-Hypaque gradient centrifugation, human monocytes (Weiner et al., *J. Immunol. Methods.* 1980, 36, 89), or the THP-1 cell line which expresses the endogenous receptor. The mixture of compound, cells and radioligand are incubated at room temperature for thirty minutes. Plates are placed onto a vacuum manifold, vacuum applied, and the plates washed three times with binding buffer containing 0.5M NaCL. The plastic skirt is removed from the plate, the plate allowed to air dry, the wells punched out and counted. The percent inhibition of binding is calculated using the total counts obtained in the absence of any competing compound and the background binding determined by addition of 100 nM MCP-1 in place of the test compound.

Antagonism of MCP-1-Induced Calcium Influx
(Sullivan et al., *Methods Mol. Biol.* 1999, 114, 125-133)

Calcium mobilization is measured using the fluorescent $Ca^{2+}$ indicator dye, Fluo-3. Cells are incubated at 8×10$^5$ cells/ml in phosphate-buffered saline containing 0.1% bovine serum albumin, 20 mM HEPES buffer, 5 mM glucose, 1% fetal bovine serum, 4 µM Fluo-3 AM and 2.5 mM probenecid for 60 minutes at 37° C. Cells used for such calcium assays can include human monocytes isolated as described by Weiner et al., *J. Immunol. Methods* 1990, 36, 89-97 or cell lines which expresses the endogenous CCR2 receptor such as THP-1 and MonoMac-6. The cells are then washed three times in phosphate-buffered saline containing 0.1% bovine serum albumin, 20 mM HEPES, 5 mM glucose and 2.5 mM probenecid. The cells are resuspended in phosphate-buffered saline containing 0.5% bovine serum albumin, 20 mM HEPES and 2.5 mM probenecid at a final concentration of 2-4×10$^6$ cells/ml. Cells are plated into 96-well, black-wall microplates (100 µl/well) and the plates centrifuged at 200×g for 5 minutes. Various concentrations of compound are added to the wells (50 µl/well) and after 5 minutes, 50 µl/well of MCP-1 is added to give a final concentration of 10 nM. Calcium mobilization is detected by using a fluorescent-imaging plate reader. The cell monolayer is excited with an argon laser (488 nM) and cell-associated fluorescence measured for 3 minutes, (every second for the first 90 seconds and every 10 seconds for the next 90 seconds). Data are generated as arbitrary fluorescence units and the change in fluorescence for each well determined as the maximum-minimum differential. Compound-dependent inhibition is calculated relative to the response of MCP-1 alone.

THP-1 Monocytic Cell Binding: Whole Cell-Based Assay

The human CCR2 binding assay was also established with the THP-1 human monocytic leukemic cell line, which expresses endogenous CCR2, using $^{125}$I-human MCP-1 as the tracer ligand. Radioligand competition binding assays were used for assessment of binding affinity of test compounds to the CCR2 receptor. For radioligand competition studies, 100 µl containing 2.5×10$^5$ THP-1 cells/well (in assay buffer containing 50 mM HEPES, pH7.4, 5 mM $MgCl_2$, 1 mM $CaCl_2$ and 0.5% BSA) were added to 96-well assay plates containing the test compounds in 3-fold serial dilution, with final concentrations ranging from 5 µM to 100 pM. Subsequently, 50 µl $^{125}$I-MCP-1 radioligand at a final concentration of 0.2 nM in assay buffer were added to the reaction. After a 90 minute incubation period at room temperature, the binding reaction was terminated by harvesting on GF/B filter plates (PerkinElmer Cat. No. 6005177) followed by washing with ice-cold wash buffer (50 mM HEPES, pH 7.4, 0.1% BSA, 0.5 M NaCl) to remove unbound ligand. After washing, the plate was dried for 45 minutes at 60° C. followed by addition of 40 µl MicroScint 20 scintillation fluid, sealed and analyzed by the Packard TopCount reader. Non-specific binding was determined in the presence of 10 µM (a molar excess of 5000 fold) of an in-house CCR2 small molecule antagonist (CCR2 $IC_{50}$=2 nM). Specific binding of $^{125}$I-MCP-1 was calculated as the difference between total and non-specific binding. The competition data was plotted as a percentage inhibition of radioligand specific bound in the absence of test compound (percent of total signal). After correcting for non-specific binding, IC50 values were determined. The IC50 is defined as the concentration of test compound required to reduce $^{125}$-MCP-1 specific binding by 50% and was calculated using the four parameter logistic equation to fit the normalized data.

Antagonism of MCP-1-induced Human PBMC Chemotaxis
(Bacon et al., *Brit. J. Pharmacol.* 1988, 95, 966)

Neuroprobe MBA96-96-well chemotaxis chamber, Polyfiltronics MPC 96 well plate, and Neuroprobe polyvinylpyrrolidone-free polycarbonate PFD5 8-micron filters are warmed in a 37° C. incubator. Human Peripheral Blood Mononuclear Cells (PBMCs) (Boyum et al., *Scand. J. Clin. Lab Invest. Suppl.* 1968, 97, 31), freshly isolated via the standard ficoll density separation method, are suspended in DMEM at 1×10$^7$ c/ml and warmed at 37° C. A 60 nM solution of human MCP-1 is also warmed at 37° C. Dilutions of test compounds are made up at 2× the concentration needed in DMEM. The PBMC suspension and the 60 nm MCP-1 solution are mixed 1:1 in polypropylene tubes with prewarmed DMEM with or without a dilution of the test compounds. These mixtures are warmed in a 37° C. tube warmer. To start the assay, add the MCP-1/compound mixture into the wells of the Polyfiltronics MPC 96 well plate that has been placed into the bottom part of the Neuroprobe chemotaxis chamber. The approximate volume is 400 µl to each well and there should be a positive meniscus after dispensing. The 8 micron filter is placed gently on top of the 96 well plate, a rubber gasket is attached to the bottom of the upper chamber, and the chamber is assembled. A 200 µl volume of the cell suspension/compound mixture is added to the appropriate wells of the upper chamber. The upper chamber is covered with a plate sealer, and the assembled unit is placed in a 37° C. incubator for 45 minutes. After incubation, the plate sealer is removed and all the remaining cell suspension is aspirated off. The chamber is disassembled and the filter gently removed. While holding the filter at a 90 degree angle, unmigrated cells are washed away using a gentle stream of phosphate buffered saline and the top of the filter wiped with the tip of a rubber squeegee. Repeat this wash twice more. The filter is air dried and then immersed completely in Wright Geimsa stain for 45 seconds. The filter is then washed by soaking in distilled water for 7 minutes, and then a 15 second additional wash in fresh distilled water. The filter is again air dried. Migrated cells on the filter are quantified by visual microscopy.

Mammalian chemokine receptors provide a target for interfering with or promoting immune cell function in a mammal, such as a human. Compounds that inhibit or promote chemokine receptor function are particularly useful for modulating immune cell function for therapeutic purposes. Accordingly, the present invention is directed to compounds which are useful in the prevention and/or treatment of a wide variety of inflammatory, infectious, and immunoregulatory disorders and diseases, including asthma and allergic diseases, infection by pathogenic microbes (which, by definition, includes viruses), as well as autoimmune pathologies such as the rheumatoid arthritis and atherosclerosis.

For example, an instant compound which inhibits one or more functions of a mammalian chemokine receptor (e.g., a human chemokine receptor) may be administered to inhibit (i.e., reduce or prevent) inflammation or infectious disease. As a result, one or more inflammatory process, such as leukocyte emigration, adhesion, chemotaxis, exocytosis (e.g., of enzymes, histamine) or inflammatory mediator release, is inhibited.

Similarly, an instant compound which promotes one or more functions of the mammalian chemokine receptor (e.g., a human chemokine) as administered to stimulate (induce or enhance) an immune or inflammatory response, such as leukocyte emigration, adhesion, chemotaxis, exocytosis (e.g., of enzymes, histamine) or inflammatory mediator release, resulting in the beneficial stimulation of inflammatory processes. For example, eosinophils can be recruited to combat parasitic infections. In addition, treatment of the aforementioned inflammatory, allergic and autoimmune diseases can also be contemplated for an instant compound which promotes one or more functions of the mammalian chemokine receptor if one contemplates the delivery of sufficient compound to cause the loss of receptor expression on cells through the induction of chemokine receptor internalization or the delivery of compound in a manner that results in the misdirection of the migration of cells.

In addition to primates, such as humans, a variety of other mammals can be treated according to the method of the present invention. For instance, mammals, including but not limited to, cows, sheep, goats, horses, dogs, cats, guinea pigs, rats or other bovine, ovine, equine, canine, feline, rodent or murine species can be treated. However, the method can also be practiced in other species, such as avian species. The subject treated in the methods above is a mammal, male or female, in whom modulation of chemokine receptor activity is desired. "Modulation" as used herein is intended to encompass antagonism, agonism, partial antagonism and/or partial agonism.

Compounds of the present invention were tested in the THP-1 monocytic binding assay described above and the results shown in Table 3 below were obtained.

TABLE 3

| Example | CCR2 Binding Ki, nM (n = 1 unless otherwise noted) |
| --- | --- |
| 1a | 983 |
| 1b | 933 |
| 1c | 736 |

TABLE 3-continued

| Example | CCR2 Binding Ki, nM (n = 1 unless otherwise noted) |
| --- | --- |
| 2a | 3510 |
| 3a | 2540 |
| 3b, diastereomer 1 | 934 |
| 3b, diastereomer 2 | 37.8 |
| 3c | 2610 |
| 3d, diastereomer 1 | 635 |
| 3d, diastereomer 2 | 173 |
| 3f, diastereomer 1 | 45.4 |
| 3f, diastereomer 2 | 11.0 |
| 3g, diastereomer 1 | 527 |
| 3g, diastereomer 2 | 10.5 +/− 3.2 (n = 2) |
| 3h, diastereomer 1 | 2130 |
| 3h, diastereomer 2 | 495 |
| 3i | 639 |
| 3j | 1280 |
| 3k | 1410 |
| 3l | 7910 |
| 3m | 153 |
| 3n | 1490 |
| 3o | 3890 |
| 3p | 23.0 |

Mammalian chemokine receptors provide a target for interfering with or promoting immune cell function in a mammal, such as a human. Compounds that inhibit or promote chemokine receptor function are particularly useful for modulating immune cell function for therapeutic purposes.

Accordingly, the present invention is directed to compounds which are useful in the prevention and/or treatment of a wide variety of inflammatory, infectious, and immunoregulatory disorders and diseases, including asthma and allergic diseases, infection by pathogenic microbes (which, by definition, includes viruses), as well as autoimmune pathologies such as the rheumatoid arthritis and atherosclerosis.

For example, an instant compound which inhibits one or more functions of a mammalian chemokine receptor (e.g., a human chemokine receptor) may be administered to inhibit (i.e., reduce or prevent) inflammation or infectious disease. As a result, one or more inflammatory process, such as leukocyte emigration, adhesion, chemotaxis, exocytosis (e.g., of enzymes, histamine) or inflammatory mediator release, is inhibited.

Similarly, an instant compound which promotes one or more functions of the mammalian chemokine receptor (e.g., a human chemokine) as administered to stimulate (induce or enhance) an immune or inflammatory response, such as leukocyte emigration, adhesion, chemotaxis, exocytosis (e.g., of enzymes, histamine) or inflammatory mediator release, resulting in the beneficial stimulation of inflammatory processes. For example, eosinophils can be recruited to combat parasitic infections. In addition, treatment of the aforementioned inflammatory, allergic and autoimmune diseases can also be contemplated for an instant compound which promotes one or more functions of the mammalian chemokine receptor if one contemplates the delivery of sufficient compound to cause the loss of receptor expression on cells through the induction of chemokine receptor internalization or the delivery of compound in a manner that results in the misdirection of the migration of cells.

In addition to primates, such as humans, a variety of other mammals can be treated according to the method of the present invention. For instance, mammals, including but not limited to, cows, sheep, goats, horses, dogs, cats, guinea pigs, rats or other bovine, ovine, equine, canine, feline, rodent or murine species can be treated. However, the method can also be practiced in other species, such as avian species. The subject treated in the methods above is a mammal, male or female, in whom modulation of chemokine receptor activity is desired. "Modulation" as used herein is intended to encompass antagonism, agonism, partial antagonism and/or partial agonism.

Diseases or conditions of human or other species which can be treated with inhibitors of chemokine receptor function, include, but are not limited to: inflammatory or allergic diseases and conditions, including respiratory allergic diseases such as asthma, allergic rhinitis, hypersensitivity lung diseases, hypersensitivity pneumonitis, eosinophilic cellulitis (e.g., Well's syndrome), eosinophilic pneumonias (e.g., Loeffler's syndrome, chronic eosinophilic pneumonia), eosinophilic fasciitis (e.g., Shulman's syndrome), delayed-type hypersensitivity, interstitial lung diseases (ILD) (e.g., idiopathic pulmonary fibrosis, or ILD associated with rheumatoid arthritis, systemic lupus erythematosus, ankylosing spondylitis, systemic sclerosis, Sjorgren's syndrome, polymyositis or dermatomyositis); systemic anaphylaxis or hypersensitivity responses, drug allergies (e.g., to penicillin, cephalosporins), eosinophilia-myalgia syndrome due to the ingestion of contaminated tryptophan, insect sting allergies; autoimmune diseases, such as rheumatoid arthritis, psoriatic arthritis, multiple sclerosis, systemic lupus erythematosus, myasthenia gravis, juvenile onset diabetes; glomerulonephritis, autoimmune thyroiditis, Behcet's disease; graft rejection (e.g., in transplantation), including allograft rejection or graft-versus-host disease; inflammatory bowel diseases, such as Crohn's disease and ulcerative colitis; spondyloarthropathies; scleroderma; psoriasis (including T-cell mediated psoriasis) and inflammatory dermatoses such as an dermatitis, eczema, atopic dermatitis, allergic contact dermatitis, urticaria; vasculitis (e.g., necrotizing, cutaneous, and hypersensitivity vasculitis); eosinophilic myositis, eosinophilic fasciitis; cancers with leukocyte infiltration of the skin or organs. Other diseases or conditions in which undesirable inflammatory responses are to be inhibited can be treated, including, but not limited to, reperfusion injury, atherosclerosis, certain hematological malignancies, cytokine-induced toxicity (e.g., septic shock, endotoxic shock), polymyositis, dermatomyositis. Infectious diseases or conditions of human or other species which can be treated with inhibitors of chemokine receptor function, include, but are not limited to, HIV.

Diseases or conditions of humans or other species which can be treated with promoters of chemokine receptor function, include, but are not limited to: immunosuppression, such as that in individuals with immunodeficiency syndromes such as AIDS or other viral infections, individuals undergoing radiation therapy, chemotherapy, therapy for autoimmune disease or drug therapy (e.g., corticosteroid therapy), which causes immunosuppression; immunosuppression due to congenital deficiency in receptor function or other causes; and infections diseases, such as parasitic diseases, including, but not limited to helminth infections, such as nematodes (round worms); (Trichuriasis, Enterobiasis, Ascariasis, Hookworm, Strongyloidiasis, Trichinosis, filariasis); trematodes (flukes) (Schistosomiasis, Clonorchiasis), cestodes (tape worms) (Echinococcosis, Taeniasis saginata, Cysticercosis); visceral worms, visceral larva migraines (e.g., Toxocara), eosinophilic gastroenteritis (e.g., *Anisaki* sp., *Phocanema* sp.), cutaneous larva migraines (*Ancylostona braziliense, Ancylostoma caninum*). The compounds of the present invention are accordingly useful in the prevention and treatment of a wide variety of inflammatory, infectious and immunoregulatory disorders and diseases.

In addition, treatment of the aforementioned inflammatory, allergic and autoimmune diseases can also be contemplated for promoters of chemokine receptor function if one contemplates the delivery of sufficient compound to cause the loss of receptor expression on cells through the induction of chemokine receptor internalization or delivery of compound in a manner that results in the misdirection of the migration of cells.

In another aspect, the instant invention may be used to evaluate the putative specific agonists or antagonists of a G protein coupled receptor. The present invention is directed to the use of these compounds in the preparation and execution of screening assays for compounds that modulate the activity of chemokine receptors. Furthermore, the compounds of this invention are useful in establishing or determining the binding site of other compounds to chemokine receptors, e.g., by competitive inhibition or as a reference in an assay to compare its known activity to a compound with an unknown activity. When developing new assays or protocols, compounds according to the present invention could be used to test their effectiveness. Specifically, such compounds may be provided in a commercial kit, for example, for use in pharmaceutical research involving the aforementioned diseases. The compounds of the instant invention are also useful for the evaluation of putative specific modulators of the chemokine receptors. In addition, one could utilize compounds of this invention to examine the specificity of G protein coupled receptors that are not thought to be chemokine receptors, either by serving as examples of compounds which do not bind or as structural variants of compounds active on these receptors which may help define specific sites of interaction.

The compounds of the present invention are used to treat or prevent disorders selected from rheumatoid arthritis, osteoarthritis, septic shock, atherosclerosis, aneurysm, fever, cardiovascular effects, haemodynamic shock, sepsis syndrome, post ischemic reperfusion injury, malaria, Crohn's disease, inflammatory bowel diseases, mycobacterial infection, meningitis, psoriasis, congestive heart failure, fibrotic diseases, cachexia, graft rejection, autoimmune diseases, skin inflammatory diseases, multiple sclerosis, radiation damage, hyperoxic alveolar injury, HIV, HIV dementia, non-insulin dependent diabetes mellitus, asthma, allergic rhinitis, atopic dermatitis, idiopathic pulmonary fibrosis, bullous pemphigoid, helminthic parasitic infections, allergic colitis, eczema, conjunctivitis, transplantation, familial eosinophilia, eosinophilic cellulitis, eosinophilic pneumonias, eosinophilic fasciitis, eosinophilic gastroenteritis, drug induced eosinophilia, cystic fibrosis, Churg-Strauss syndrome, lymphoma, Hodgkin's disease, colonic carcinoma, Felty's syndrome, sarcoidosis, uveitis, Alzheimer, Glomerulonephritis, and systemic lupus erythematosus.

In another aspect, the compounds are used to treat or prevent inflammatory disorders selected from rheumatoid arthritis, osteoarthritis, atherosclerosis, aneurysm, fever, cardiovascular effects, Crohn's disease, inflammatory bowel diseases, psoriasis, congestive heart failure, multiple sclerosis, autoimmune diseases, skin inflammatory diseases.

In another aspect, the compounds are used to treat or prevent inflammatory disorders selected from rheumatoid arthritis, osteoarthritis, atherosclerosis, Crohn's disease, inflammatory bowel diseases, and multiple sclerosis.

Combined therapy to prevent and treat inflammatory, infectious and immunoregulatory disorders and diseases, including asthma and allergic diseases, as well as autoimmune pathologies such as rheumatoid arthritis and atherosclerosis, and those pathologies noted above is illustrated by the combination of the compounds of this invention and other compounds which are known for such utilities. For example, in the treatment or prevention of inflammation, the present compounds may be used in conjunction with an anti-inflammatory or analgesic agent such as an opiate agonist, a lipoxygenase inhibitor, a cyclooxygenase-2 inhibitor, an interleukin inhibitor, such as an interleukin-1 inhibitor, a tumor necrosis factor inhibitor, an NMDA antagonist, an inhibitor nitric oxide or an inhibitor of the synthesis of nitric oxide, a non-steroidal anti-inflammatory agent, a phosphodiesterase inhibitor, or a cytokine-suppressing anti-inflammatory agent, for example with a compound such as acetaminophen, aspirin, codeine, fentaynI, ibuprofen, indomethacin, ketorolac, morphine, naproxen, phenacetin, piroxicam, a steroidal analgesic, sufentanyl, sunlindac, interferon alpha and the like. Similarly, the instant compounds may be administered with a pain reliever; a potentiator such as caffeine, an H2-antagonist, simethicone, aluminum or magnesium hydroxide; a decongestant such as phenylephrine, phenylpropanolamine, pseudophedrine, oxymetazoline, ephinephrine, naphazoline, xylometazoline, propylhexedrine, or levodesoxy-ephedrine; and antitussive such as codeine, hydrocodone, caramiphen, carbetapentane, or dextramethorphan; a diuretic; and a sedating or non-sedating antihistamine. Likewise, compounds of the present invention may be used in combination with other drugs that are used in the treatment/prevention/suppression or amelioration of the diseases or conditions for which compound of the present invention are useful. Such other drugs may be administered, by a route and in an amount commonly used therefore, contemporaneously or sequentially with a compound of the present invention. When a compound of the present invention is used contemporaneously with one or more other drugs, a pharmaceutical composition containing such other drugs in addition to the compound of the present invention may be used. Accordingly, the pharmaceutical compositions of the present invention include those that also contain one or more other active ingredients, in addition to a compound of the present invention.

Examples of other active ingredients that may be combined with a compound of the present invention, either administered separately or in the same pharmaceutical compositions, include, but are not limited to: (a) integrin antagonists such as those for selectins, ICAMs and VLA-4; (b) steroids such as beclomethasone, methylprednisolone, betamethasone, prednisone, dexamethasone, and hydrocortisone; (c) immunosuppressants such as cyclosporin, tacrolimus, rapamycin and other FK-506 type immunosuppressants; (d) antihistamines (H1-histamine antagonists) such as bromopheniramine, chlorpheniramine, dexchlorpheniramine, triprolidine, clemastine, diphenhydramine, diphenylpyraline, tripelennamine, hydroxyzine, methdilazine, promethazine, trimeprazine, azatadine, cyproheptadine, antazoline, pheniramine pyrilamine, astemizole, terfenadine, loratadine, cetirizine, fexofenadine, descarboethoxyloratadine, and the like; (e) non-steroidal anti-asthmatics such as b2-agonists (terbutaline, metaproterenol, fenoterol, isoetharine, albuteral, bitolterol, and pirbuterol), theophylline, cromolyn sodium, atropine, ipratropium bromide, leukotriene antagonists (zafirlukast, montelukast, pranlukast, iralukast, pobilukast, SKB-102, 203), leukotriene biosynthesis inhibitors (zileuton, BAY-1005); (f) non-steroidal anti-inflammatory agents (NSAIDs) such as propionic acid derivatives (alminoprofen, benxaprofen, bucloxic acid, carprofen, fenbufen, fenoprofen, fluprofen, flurbiprofen, ibuprofen, indoprofen, ketoprofen, miroprofen, naproxen, oxaprozin, pirprofen, pranoprofen, suprofen, tiaprofenic acid, and tioxaprofen), acetic acid derivatives (indomethacin, acemetacin, alclofenac, clidanac, diclofenac, fenclofenac, fenclozic acid, fentiazac, furofenac, ibufenac, isoxepac, oxpinac, sulindac, tiopinac, tolmetin, zidometacin, and zomepirac), fenamic acid derivatives (flufenamic acid, meclofenamic acid, mefenamic acid, niflumic acid and tolfenamic acid), biphenylcarboxylic acid derivatives (diflunisal and flufenisal), oxicams (isoxicam, piroxicam, sudoxicam and tenoxican), salicylates (acetyl salicylic acid, sulfasalazine) and the pyrazolones (apazone, bezpiperylon, feprazone, mofebutazone, oxyphenbutazone, phenylbutazone); (g) cyclooxygenase-2 (COX-2) inhibitors; (h) inhibitors of phosphodiesterase type IV (PDE-IV); (i) other antagonists of the chemokine receptors; (j) cholesterol lowering agents such as HMG-COA reductase inhibitors (lovastatin, simvastatin and pravastatin, fluvastatin, atorvastatin, and other statins), sequestrants (cholestyramine and colestipol), nicotonic acid, fenofibric acid derivatives (gemfibrozil, clofibrat, fenofibrate and benzafibrate), and probucol; (k) anti-diabetic agents such as insulin, sulfony ureas, biguanides (metformin), a-glucosidase inhibitors (acarbose) and glitazones (troglitazone and pioglitazone); (l) preparations of interferons (interferon alpha-2a, interferon-2B, interferon alpha-N3, interferon beta-1a, interferon beta-1b, interferon gamma-b); (m) antiviral compounds such as efavirenz, nevirapine, indinavir, ganciclovir, lamivudine, famciclovir, and zalcitabine; (n) other compound such as 5-aminosalicylic acid an prodrugs thereof, anti-metabolites such as azathioprine and 6-mercaptopurine, and cytotoxic cancer chemotherapeutic agents. The weight ratio of the compound of the present invention to the second active ingredient may be varied and will depend upon the effective doses of each ingredient.

Generally, an effective dose of each will be used. Thus, for example, when a compound of the present invention is combined with an NSAID the weight ratio of the compound of the present invention to the NSAID will generally range from about 1000:1 to about 1:1000, or alternatively from about 200:1 to about 1:200. Combinations of a compound of the present invention and other active ingredients will generally also be within the aforementioned range, but in each case, an effective dose of each active ingredient should be used.

The compounds are administered to a mammal in a therapeutically effective amount. By "therapeutically effective amount" it is meant an amount of a compound of Formula I that, when administered alone or in combination with an additional therapeutic agent to a mammal, is effective to prevent or ameliorate the thromboembolic disease condition or the progression of the disease.

Dosage and Formulation

The compounds of this invention can be administered in such oral dosage forms as tablets, capsules (each of which includes sustained release or timed release formulations), pills, powders, granules, elixirs, tinctures, suspensions, syrups, and emulsions. They may also be administered in intravenous (bolus or infusion), intraperitoneal, subcutaneous, or intramuscular form, all using dosage forms well known to those of ordinary skill in the pharmaceutical arts. They can be administered alone, but generally will be administered with a pharmaceutical carrier selected on the basis of the chosen route of administration and standard pharmaceutical practice.

The dosage regimen for the compounds of the present invention will, of course, vary depending upon known factors, such as the pharmacodynamic characteristics of the particular agent and its mode and route of administration; the species, age, sex, health, medical condition, and weight of the recipient; the nature and extent of the symptoms; the kind of concurrent treatment; the frequency of treatment; the route of administration, the renal and hepatic function of the patient, and the effect desired. A physician or veterinarian can determine and prescribe the effective amount of the drug required to prevent, counter, or arrest the progress of the thromboembolic disorder.

By way of general guidance, the daily oral dosage of each active ingredient, when used for the indicated effects, will range between about 0.001 to 1000 mg/kg of body weight, or between about 0.01 to 100 mg/kg of body weight per day, or alternatively, between about 1.0 to 20 mg/kg/day. Intravenously, the doses will range from about 1 to about 10 mg/kg/minute during a constant rate infusion. Compounds of this invention may be administered in a single daily dose, or the total daily dosage may be administered in divided doses of two, three, or four times daily.

Compounds of this invention can be administered in intranasal form via topical use of suitable intranasal vehicles, or via transdermal routes, using transdermal skin patches. When administered in the form of a transdermal delivery system, the dosage administration will, of course, be continuous rather than intermittent throughout the dosage regimen.

The compounds are typically administered in admixture with suitable pharmaceutical diluents, excipients, or carriers (collectively referred to herein as pharmaceutical carriers) suitably selected with respect to the intended form of administration, that is, oral tablets, capsules, elixirs, syrups and the like, and consistent with conventional pharmaceutical practices.

For instance, for oral administration in the form of a tablet or capsule, the active drug component can be combined with an oral, non-toxic, pharmaceutically acceptable, inert carrier such as lactose, starch, sucrose, glucose, methyl cellulose, magnesium stearate, dicalcium phosphate, calcium sulfate, mannitol, sorbitol and the like; for oral administration in liquid form, the oral drug components can be combined with any oral, non-toxic, pharmaceutically acceptable inert carrier such as ethanol, glycerol, water, and the like. Moreover, when desired or necessary, suitable binders, lubricants, disintegrating agents, and coloring agents can also be incorporated into the mixture. Suitable binders include starch, gelatin, natural sugars such as glucose or beta-lactose, corn sweeteners, natural and synthetic gums such as acacia, tragacanth, or sodium alginate, carboxymethylcellulose, polyethylene glycol, waxes, and the like. Lubricants used in these dosage forms include sodium oleate, sodium stearate, magnesium stearate, sodium benzoate, sodium acetate, sodium chloride, and the like. Disintegrators include, without limitation, starch, methyl cellulose, agar, bentonite, xanthan gum, and the like.

The compounds of the present invention can also be administered in the form of liposome delivery systems, such as small unilamellar vesicles, large unilamellar vesicles, and multilamellar vesicles. Liposomes can be formed from a variety of phospholipids, such as cholesterol, stearylamine, or phosphatidylcholines.

Compounds of the present invention may also be coupled with soluble polymers as targetable drug carriers. Such polymers can include polyvinylpyrrolidone, pyran copolymer, polyhydroxypropylmethacrylamide-phenol, polyhydroxyethylaspartamidephenol, or polyethyleneoxide-polylysine substituted with palmitoyl residues. Furthermore, the compounds of the present invention may be coupled to a class of biodegradable polymers useful in achieving controlled release of a drug, for example, polylactic acid, polyglycolic acid, copolymers of polylactic and polyglycolic acid, poly-epsilon caprolactone, polyhydroxy butyric acid, polyorthoesters, polyacetals, polydihydropyrans, polycyanoacylates, and crosslinked or amphipathic block copolymers of hydrogels.

Dosage forms (pharmaceutical compositions) suitable for administration may contain from about 1 milligram to about 100 milligrams of active ingredient per dosage unit. In these pharmaceutical compositions the active ingredient will ordinarily be present in an amount of about 0.5-95% by weight based on the total weight of the composition.

Gelatin capsules may contain the active ingredient and powdered carriers, such as lactose, starch, cellulose derivatives, magnesium stearate, stearic acid, and the like. Similar diluents can be used to make compressed tablets. Both tablets and capsules can be manufactured as sustained release products to provide for continuous release of medication over a period of hours. Compressed tablets can be sugar coated or film coated to mask any unpleasant taste and protect the tablet from the atmosphere, or enteric coated for selective disintegration in the gastrointestinal tract.

Liquid dosage forms for oral administration can contain coloring and flavoring to increase patient acceptance.

In general, water, suitable oil, saline, aqueous dextrose (glucose), and related sugar solutions and glycols such as propylene glycol or polyethylene glycols are suitable carriers for parenteral solutions. Solutions for parenteral administration may contain a water soluble salt of the active ingredient, suitable stabilizing agents, and if necessary, buffer substances. Antioxidizing agents such as sodium bisulfite, sodium sulfite, or ascorbic acid, either alone or combined, are suitable stabilizing agents. Also used are citric acid and its salts and sodium EDTA. In addition, parenteral solutions can contain preservatives, such as benzalkonium chloride, methyl- or propyl-paraben, and chlorobutanol.

Suitable pharmaceutical carriers are described in *Remington's Pharmaceutical Sciences* (Mack Publishing Company), a standard reference text in this field.

Representative useful pharmaceutical dosage-forms for administration of the compounds of this invention can be illustrated as follows:

Capsules

A large number of unit capsules can be prepared by filling standard two-piece hard gelatin capsules each with 100 milligrams of powdered active ingredient, 150 milligrams of lactose, 50 milligrams of cellulose, and 6 milligrams magnesium stearate.

Soft Gelatin Capsules

A mixture of active ingredient in a digestible oil such as soybean oil, cottonseed oil or olive oil may be prepared and injected by means of a positive displacement pump into gelatin to form soft gelatin capsules containing 100 milligrams of the active ingredient. The capsules should be washed and dried.

Tablets

Tablets may be prepared by conventional procedures so that the dosage unit is 100 milligrams of active ingredient, 0.2 milligrams of colloidal silicon dioxide, milligrams of magnesium stearate, 275 milligrams of microcrystalline cellulose, 11 milligrams of starch and 98.8 milligrams of lactose. Appropriate coatings may be applied to increase palatability or delay absorption.

Injectable

A parenteral composition suitable for administration by injection may be prepared by stirring 1.5% by weight of active ingredient in 10% by volume propylene glycol and water. The solution should be made isotonic with sodium chloride and sterilized.

Suspension

An aqueous suspension can be prepared for oral administration so that each 5 mL contain 100 mg of finely divided active ingredient, 200 mg of sodium carboxymethyl cellulose, 5 mg of sodium benzoate, 1.0 g of sorbitol solution, U.S.P., and 0.025 mL of vanillin.

Where the compounds of this invention are combined with other anticoagulant agents, for example, a daily dosage may be about 0.1 to 100 milligrams of the compound of Formula I and about 1 to 7.5 milligrams of the second anticoagulant, per kilogram of patient body weight. For a tablet dosage form, the compounds of this invention generally may be present in an amount of about 5 to 10 milligrams per dosage unit, and the second anti-coagulant in an amount of about 1 to milligrams per dosage unit.

Where two or more of the foregoing second therapeutic agents are administered with the compound of Formula I, generally the amount of each component in a typical daily dosage and typical dosage form may be reduced relative to the usual dosage of the agent when administered alone, in view of the additive or synergistic effect of the therapeutic agents when administered in combination. Particularly when provided as a single dosage unit, the potential exists for a chemical interaction between the combined active ingredients. For this reason, when the compound of Formula I and a second therapeutic agent are combined in a single dosage unit they are formulated such that although the active ingredients are combined in a single dosage unit, the physical contact between the active ingredients is minimized (that is, reduced). For example, one active ingredient may be enteric coated. By enteric coating one of the active ingredients, it is possible not only to minimize the contact between the combined active ingredients, but also, it is possible to control the release of one of these components in the gastrointestinal tract such that one of these components is not released in the stomach but rather is released in the intestines. One of the active ingredients may also be coated with a material which affects a sustained-release throughout the gastrointestinal tract and also serves to minimize physical contact between the combined active ingredients. Furthermore, the sustained-released component can be additionally enteric coated such that the release of this component occurs only in the intestine. Still another approach would involve the formulation of a combination product in which the one component is coated with a sustained and/or enteric release polymer, and the other component is also coated with a polymer such as a low-viscosity grade of hydroxypropyl methylcellulose (HPMC) or other appropriate materials as known in the art, in order to further separate the active components. The polymer coating serves to form an additional barrier to interaction with the other component.

These as well as other ways of minimizing contact between the components of combination products of the present invention, whether administered in a single dosage form or administered in separate forms but at the same time by the same manner, will be readily apparent to those skilled in the art, once armed with the present disclosure.

While the invention has been described in detail and with reference to specific embodiments thereof, it will be apparent to one skilled in the art that various changes and modifications can be made therein without departing from the spirit and scope thereof.

What is claimed is:

1. A compound of formula (I):

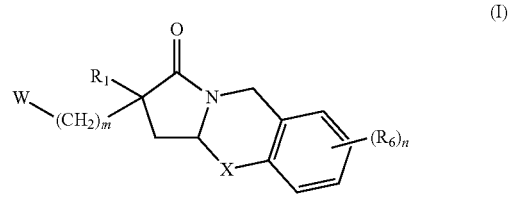

or a stereoisomer or a pharmaceutically acceptable salt thereof, wherein:

X is O;

W is a —$NR_2R_3$ or a 3- to 20-membered nitrogen containing ring, wherein the ring is (i) attached through the nitrogen atom, (ii) may optionally contain 1-4 heteroatoms selected from N, O, and S and (iii) be optionally substituted with one or more $R_{10a}$'s;

m is 1-4;

n is 0-2;

$R_1$ is H or alkyl;

$R_2$ is H, alkyl, cycloalkyl, aryl, heteroaryl or heterocyclyl, wherein the cycloalkyl, aryl, heteroaryl or heterocyclyl may be optionally substituted with may be optionally substituted with be optionally substituted with one or more $R_{9a}$'s;

$R_3$ is H, alkyl, cycloalkyl, aryl, heteroaryl or heterocyclyl, wherein the cycloalkyl, aryl, heteroaryl or heterocyclyl may be optionally substituted with may be optionally substituted with be optionally substituted with one or more $R_{9a}$'s;

$R_6$, at each occurrence, is independently selected from halo, alkyl, haloalkyl, haloalkoxy, and aryl optionally substituted with halo;

$R_{9a}$, at each occurrence, is independently selected from alkyl, haloalkyl, aryl, cycloalkyl, heteroaryl, heterocyclyl, halo, —CN, —$NO_2$, —C(=O)$OR_{14}$, —$OCF_3$, —$OR_{14}$, =O, —$NR_{14}R_{14}$ or arylalkyl;

$R_{10a}$, at each occurrence, is independently selected from alkyl, haloalkyl, aryl, cycloalkyl, heteroaryl, heterocyclyl, halo, —CN, —$NO_2$, —C(=O)$OR_{14}$, —$OCF_3$, —$OR_{14}$, =O, —$NR_{14}R_{14}$ or arylalkyl, wherein the aryl, cycloalkyl, heteroaryl, and heterocyclyl may be optionally substituted with on or more $R_{14a}$'S;

$R_{14}$, at each occurrence, is independently selected from hydrogen, alkyl, cycloalkyl, aryl, heteroaryl or heterocyclyl, wherein the alkyl, cycloalkyl, aryl, heteroaryl and heterocyclyl may be optionally substituted with be optionally substituted with 0-3 $R_{14a}$;

$R_{14a}$, at each occurrence, is independently selected from alkyl, haloalkyl, aryl, cycloalkyl, heteroaryl, heterocyclyl, halo, —CN, —$NO_2$, —C(=O)$OR_{24}$, —$OCF_3$, —$OR_{24}$, =O, —$NR_{24}R_{24}$ or arylalkyl; and $R_{24}$, at each occurrence, is independently selected from hydrogen, alkyl, cycloalkyl, aryl, heteroaryl or heterocyclyl.

2. The compound of claim 1, wherein the compound is a compound of formula (Ia):

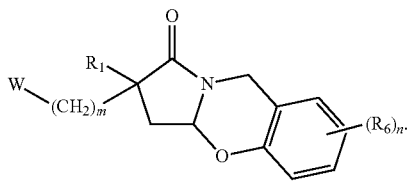

(Ia)

3. The compound, enantiomer, diastereomer, or salt thereof, of claim 1, wherein:

X is O;

W is a —$NR_2R_3$ or a 3- to 15-membered nitrogen containing ring, wherein the ring is (i) attached through the nitrogen atom, (ii) may optionally contain 1-4 heteroatoms selected from N, O, and S and (iii) be optionally substituted with one or more $R_{10a}$'s;

m is 1-3;

n is 0-2;

$R_1$ is H or alkyl;

$R_2$ is H, alkyl, cycloalkyl, aryl or heterocyclyl, wherein the cycloalkyl, aryl or heterocyclyl may be optionally substituted with may be optionally substituted with be optionally substituted with one or more $R_{9a}$'s;

$R_3$ is H, alkyl, cycloalkyl, aryl or heterocyclyl, wherein the cycloalkyl, aryl or heterocyclyl may be optionally substituted with may be optionally substituted with be optionally substituted with one or more $R_{9a}$'s;

$R_6$, at each occurrence, is independently selected from halo, alkyl, haloalkyl, haloalkoxy, and aryl optionally substituted with halo;

$R_{9a}$, at each occurrence, is independently selected from alkyl, haloalkyl, aryl, cycloalkyl, heteroaryl, heterocyclyl, halo, —CN, —$NO_2$, —C(=O)$OR_{14}$, —$OCF_3$, —$OR_{14}$, =O, or arylalkyl;

$R_{10a}$, at each occurrence, is independently selected from alkyl, haloalkyl, aryl, cycloalkyl, heteroaryl, heterocyclyl, halo, —CN, —$NO_2$, —C(=O)$OR_{14}$, —$OCF_3$, —$OR_{14}$, =O, or arylalkyl, wherein the aryl, cycloalkyl, heteroaryl, and heterocyclyl may be optionally substituted with on or more $R_{14a}$'S;

$R_{14}$, at each occurrence, is independently selected from hydrogen, alkyl, cycloalkyl, aryl, heteroaryl or heterocyclyl, wherein the alkyl, cycloalkyl, aryl, heteroaryl and heterocyclyl may be optionally substituted with be optionally substituted with 0-3 $R_{14a}$;

$R_{14a}$, at each occurrence, is independently selected from alkyl, haloalkyl, aryl, cycloalkyl, heteroaryl, heterocyclyl, halo, —CN, —$NO_2$, —C(=O)$OR_{24}$, —$OCF_3$, —$OR_{24}$, =O, or arylalkyl; and $R_{24}$, at each occurrence, is independently selected from hydrogen, alkyl, cycloalkyl, aryl, heteroaryl or heterocyclyl.

4. The compound, enantiomer, diastereomer, or salt thereof, of claim 1, wherein:

X is O;

W is a —$NR_2R_3$ or a 3- to 12-membered nitrogen containing ring, wherein the ring is (i) attached through the nitrogen atom, (ii) may optionally contain 1-4 heteroatoms selected from N, O, and S and (iii) be optionally substituted with one or more $R_{10a}$'s;

m is 1-2;

n is 1-2;

$R_1$ is H or alkyl;

$R_2$ is H, alkyl or cycloalkyl, wherein the cycloalkyl may be optionally substituted with may be optionally substituted with be optionally substituted with one or more $R_{9a}$'S;

$R_3$ is H, alkyl or cycloalkyl, wherein the cycloalkyl may be optionally substituted with may be optionally substituted with be optionally substituted with one or more $R_{9a}$'s;

$R_6$, at each occurrence, is independently selected from halo, alkyl, haloalkyl, haloalkoxy, and aryl optionally substituted with halo;

$R_{9a}$, at each occurrence, is independently selected from alkyl, haloalkyl, aryl, cycloalkyl, heteroaryl, heterocyclyl, halo, —CN, —$NO_2$, —C(=O)$OR_{14}$, —$OCF_3$, —$OR_{14}$, or arylalkyl;

$R_{10a}$, at each occurrence, is independently selected from alkyl, haloalkyl, aryl, cycloalkyl, heteroaryl, heterocyclyl, halo, —CN, —$NO_2$, —C(=O)$OR_{14}$, —$OCF_3$, —$OR_{14}$, or arylalkyl, wherein the aryl, cycloalkyl, heteroaryl, and heterocyclyl may be optionally substituted with on or more $R_{14a}$'s;

$R_{14}$, at each occurrence, is independently selected from hydrogen, alkyl, cycloalkyl, aryl or heteroaryl, wherein the alkyl, cycloalkyl, aryl and heteroaryl may be optionally substituted with be optionally substituted with 0-3 $R_{14a}$;

$R_{14a}$, at each occurrence, is independently selected from alkyl, haloalkyl, aryl, cycloalkyl, heteroaryl, heterocyclyl, halo, —CN, —$NO_2$, —C(=O)$OR_{24}$, —$OCF_3$, —$OR_{24}$ or arylalkyl; and $R_{24}$, at each occurrence, is independently selected from hydrogen, alkyl, cycloalkyl, aryl or heteroaryl.

5. The compound, enantiomer, diastereomer, or salt thereof, of claim 1, wherein:

X is O;

W is a —$NR_2R_3$ or a 3- to 12-membered nitrogen containing ring, wherein the ring is (i) attached through the nitrogen atom, (ii) may optionally contain 1-4 heteroatoms selected from N, O, and S and (iii) be optionally substituted with one or more $R_{10a}$'s;

m is 1-2;

n is 1-2;

$R_1$ is H or alkyl;

$R_2$ is H, alkyl or cycloalkyl, wherein the cycloalkyl may be optionally substituted with may be optionally substituted with be optionally substituted with one or more $R_{9a}$'s;

$R_3$ is H, alkyl or cycloalkyl, wherein the cycloalkyl may be optionally substituted with may be optionally substituted with be optionally substituted with one or more $R_{9a}$'s;

$R_6$, at each occurrence, is independently selected from halo, alkyl, haloalkyl, haloalkoxy, and aryl optionally substituted with halo;

$R_{9a}$, at each occurrence, is independently selected from alkyl, haloalkyl, aryl, cycloalkyl, heteroaryl, heterocyclyl, halo, —CN, —$NO_2$, —C(=O)$OR_{14}$, —$OCF_3$, —$OR_{14}$, or arylalkyl;

$R_{10a}$, at each occurrence, is independently selected from alkyl, haloalkyl, aryl, cycloalkyl, heteroaryl, heterocyclyl, halo, —CN, —$NO_2$, —C(=O)$OR_{14}$, —$OCF_3$, —$OR_{14}$, or arylalkyl, wherein the aryl, cycloalkyl, heteroaryl, and heterocyclyl may be optionally substituted with on or more $R_{14a}$'S;

$R_{14}$, at each occurrence, is independently selected from hydrogen, alkyl, cycloalkyl, aryl or heteroaryl, wherein the alkyl, cycloalkyl, aryl and heteroaryl may be optionally substituted with be optionally substituted with 0-3 $R_{14a}$;

$R_{14a}$, at each occurrence, is independently selected from alkyl, haloalkyl, aryl, cycloalkyl, heteroaryl, heterocyclyl, halo, —CN, —NO$_2$, —C(=O)OR$_{24}$, —OCF$_3$, —OR$_{24}$ or arylalkyl; and $R_{24}$, at each occurrence, is independently selected from hydrogen, alkyl, cycloalkyl, aryl or heteroaryl.

6. The compound, enantiomer, diastereomer, or salt thereof, of claim 1, wherein:

X is O;

W is a 3- to 12-membered nitrogen containing ring, wherein the ring is (i) attached through the nitrogen atom, (ii) may optionally contain 1-4 heteroatoms selected from N, O, and S and (iii) be optionally substituted with one or more $R_{10a}$'s;

m is 1-2;

n is 1-2;

$R_1$ is H or alkyl;

$R_6$, at each occurrence, is independently selected from halo, alkyl, haloalkyl, haloalkoxy, and aryl optionally substituted with halo;

$R_{10a}$, at each occurrence, is independently selected from alkyl, haloalkyl, aryl, cycloalkyl, heteroaryl, heterocyclyl, halo, —CN, —NO$_2$, —C(=O)OR$_{14}$, —OCF$_3$, —OR$_{14}$, or arylalkyl, wherein the aryl, cycloalkyl, heteroaryl, heterocyclyl may be optionally substituted with on or more $R_{14a}$'S;

$R_{14}$, at each occurrence, is independently selected from hydrogen, alkyl, cycloalkyl, aryl or heteroaryl, wherein the alkyl, cycloalkyl, aryl and heteroaryl may be optionally substituted with be optionally substituted with 0-3 $R_{14a}$;

$R_{14a}$, at each occurrence, is independently selected from alkyl, haloalkyl, aryl, cycloalkyl, heteroaryl, heterocyclyl, halo, —CN, —NO$_2$, —C(=O)OR$_{24}$, —OCF$_3$, —OR$_{24}$ or arylalkyl; and $R_{24}$, at each occurrence, is independently selected from hydrogen, alkyl, cycloalkyl, aryl or heteroaryl.

7. The compound, enantiomer, diastereomer, or salt thereof, of claim 1, wherein:

X is O;

W is a 5- to 12-membered nitrogen containing ring, wherein the ring is (i) attached through the nitrogen atom, (ii) may optionally contain 1-4 heteroatoms selected from N, O, and S and (iii) be optionally substituted with one or more $R_{10a}$'s;

m is 1-2;

n is 1-2;

$R_1$ is H or alkyl;

$R_6$, at each occurrence, is independently selected from halo, alkyl, haloalkyl, haloalkoxy, and aryl optionally substituted with halo;

$R_{10a}$, at each occurrence, is independently selected from alkyl, haloalkyl, aryl, cycloalkyl, heteroaryl, halo, —CN, —NO$_2$, —C(=O)OR$_{14}$, —OCF$_3$, —OR$_{14}$, or arylalkyl, wherein the aryl, cycloalkyl and heteroaryl may be optionally substituted with on or more $R_{14a}$'s;

$R_{14}$, at each occurrence, is independently selected from hydrogen, alkyl, cycloalkyl, aryl or heteroaryl, wherein the alkyl, cycloalkyl, aryl and heteroaryl may be optionally substituted with be optionally substituted with 0-3 $R_{14a}$;

$R_{14a}$, at each occurrence, is independently selected from alkyl, haloalkyl, aryl, cycloalkyl, heteroaryl, halo, —CN, —NO$_2$, —C(=O)OR$_{24}$, —OCF$_3$, —OR$_{24}$ or arylalkyl; and $R_{24}$, at each occurrence, is independently selected from hydrogen, alkyl, cycloalkyl, aryl or heteroaryl.

8. The compound, enantiomer, diastereomer, or salt thereof, of claim 1, wherein:

X is O;

W is a 5- or 6-membered nitrogen containing ring, wherein the ring is (i) attached through the nitrogen atom, (ii) may optionally contain 1-3 heteroatoms selected from N, O, and S and (iii) be optionally substituted with one or more $R_{10a}$'s;

m is 2;

n is 1-2;

$R_1$ is H or alkyl;

$R_6$, at each occurrence, is independently selected from halo, alkyl, haloalkyl, haloalkoxy, and aryl optionally substituted with halo;

$R_{10a}$, at each occurrence, is independently selected from alkyl, haloalkyl, aryl, cycloalkyl, heteroaryl, halo, —C(=O)OR$_{14}$, —OCF$_3$, —OR$_{14}$, or arylalkyl, wherein the aryl, cycloalkyl and heteroaryl may be optionally substituted with on or more $R_{14a}$'s;

$R_{14}$, at each occurrence, is independently selected from hydrogen, alkyl, cycloalkyl or aryl, wherein the alkyl, cycloalkyl and aryl may be optionally substituted with be optionally substituted with 0-3 $R_{14a}$;

$R_{14a}$, at each occurrence, is independently selected from alkyl, haloalkyl, aryl, cycloalkyl, heteroaryl, halo, —C(=O)OR$_{24}$, —OCF$_3$, —OR$_{24}$ or arylalkyl; and $R_{24}$, at each occurrence, is independently selected from hydrogen, alkyl, cycloalkyl, or aryl.

9. The compound, enantiomer, diastereomer, or salt thereof, of claim 1, wherein:

X is O;

W is pyrrolidinyl, piperazinyl or piperidinyl, wherein the ring is (i) attached through a nitrogen atom and may be optionally substituted with one or more $R_{10a}$'s;

m is 2;

n is 1-2;

$R_1$ is H or isopropyl;

$R_6$, at each occurrence, is independently selected from Cl, Br, F, t-butyl, —CF$_3$, —CF$_2$CF$_3$, —OCF$_3$, and phenyl optionally substituted with Cl, Br, F or I;

$R_{10a}$, at each occurrence, is independently selected from methyl, —CF$_3$, —CF$_2$CF$_3$, aryl, Cl, F, Br, —C(=O)OH, —OCF$_3$, —OH or benzyl.

10. A compound, enantiomer, diastereomer, or salt thereof, selected from the group consisting of:

55
-continued
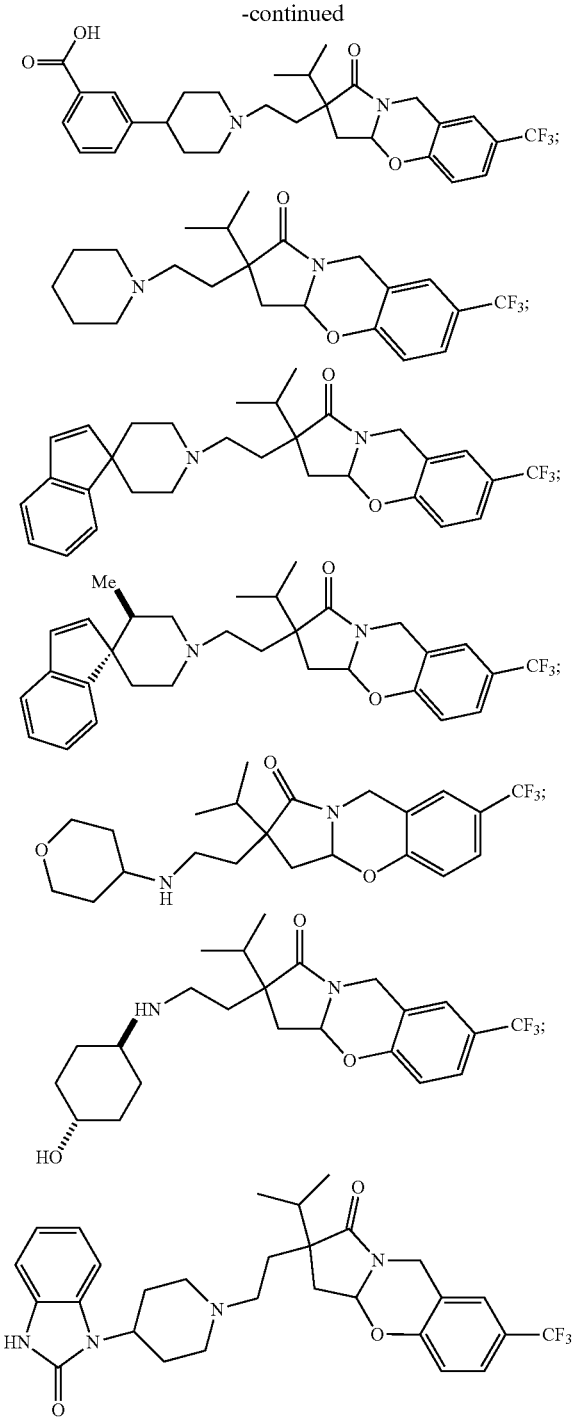
56
-continued
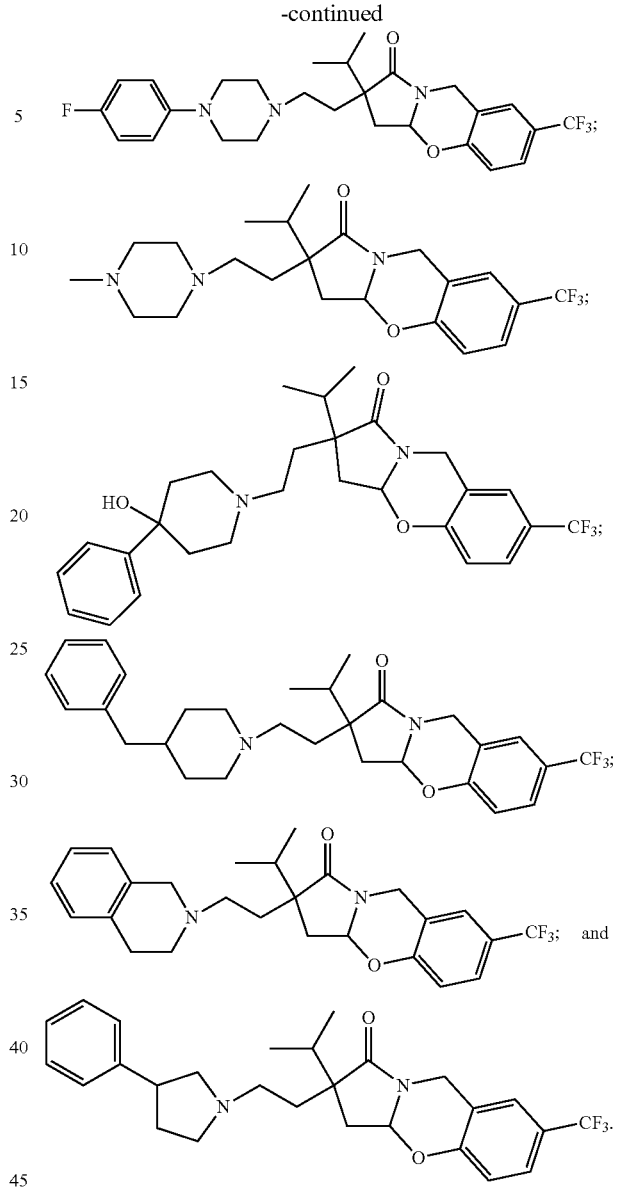
11. A pharmaceutical composition comprised of a pharmaceutically acceptable carrier and a therapeutically effective amount of the compound of claim 1.
12. A pharmaceutical composition comprised of a pharmaceutically acceptable carrier and a therapeutically effective amount of the compound of claim 10.
* * * * *